(12) United States Patent  
Rahimi

(10) Patent No.: US 8,570,175 B2
(45) Date of Patent: Oct. 29, 2013

(54) SECURELY ATTACHABLE MONITORING DEVICE

(76) Inventor: Gil Goel Rahimi, Nazareth Elit (IL)

(*) Notice: Subject to any disclaimer, the term of this patent is extended or adjusted under 35 U.S.C. 154(b) by 741 days.

(21) Appl. No.: 12/744,788

(22) PCT Filed: Oct. 2, 2008

(86) PCT No.: PCT/IL2008/001313
§ 371 (c)(1),
(2), (4) Date: May 26, 2010

(87) PCT Pub. No.: WO2009/069115
PCT Pub. Date: Jun. 4, 2009

(65) Prior Publication Data
US 2012/0299730 A1   Nov. 29, 2012

Related U.S. Application Data

(60) Provisional application No. 60/990,160, filed on Nov. 26, 2007.

(51) Int. Cl.
*G08B 21/02* (2006.01)

(52) U.S. Cl.
USPC .............. 340/572.9; 340/572.8; 340/573.1; 340/604

(58) Field of Classification Search
USPC ........ 340/906, 907, 909, 572.8, 572.9, 573.1, 340/604
See application file for complete search history.

(56) References Cited

U.S. PATENT DOCUMENTS

| 5,469,146 | A  | * | 11/1995 | Gurler ........................... 340/605 |
| 5,568,128 | A  | * | 10/1996 | Nair ............................ 340/573.5 |
| 7,136,479 | B2 | * | 11/2006 | Gutta et al. .............. 379/266.01 |
| 7,250,547 | B1 |   | 7/2007  | Hofmeister et al. |
| 2002/0057202 | A1 | * | 5/2002 | Luzon ......................... 340/573.1 |
| 2005/0184870 | A1 | * | 8/2005 | Galperin et al. ........... 340/568.2 |
| 2008/0272918 | A1 | * | 11/2008 | Ingersoll .................... 340/573.1 |

FOREIGN PATENT DOCUMENTS

WO   2006118913  A1   11/2006

* cited by examiner

*Primary Examiner* — Daniel Wu
*Assistant Examiner* — Benyam Haile
(74) *Attorney, Agent, or Firm* — Browdy and Neimark PLLC

(57) ABSTRACT

The present invention relates to a device for monitoring the condition of a person, which comprises: (a) a casing; (b) electronic circuitry; and (c) at least one secure attachment mechanism, each comprising a first member which is capable of moving in a forward direction up to a locking state, at which it is interlocked by at least one second member, so that said first member cannot be moved backward by applying a first backward force, unless said interlock is unlocked, by applying at least one second force, independent of said first force. Preferably, said first member is a spike having at least one recess, wherein at said locking state said second member is introduced into said recess, thereby preventing said spike from moving backward.

20 Claims, 20 Drawing Sheets

Monitoring Device

Remote Device

SECURELY ATTACHABLE MONITORING DEVICE

FIELD OF THE INVENTION

The present invention is in the technical field of monitoring the condition of a person. More specifically, the invention suggests secure mechanisms for attaching such devices to clothing and bedding articles.

BACKGROUND OF THE INVENTION

Definition: The present invention relates to monitoring devices attachable to diapers, toilet training pants, pajamas, garments and undergarments, articles of bedding, feminine care articles and bandages. For the purpose of clarity, throughout this application, articles to which said devices are attached, will be referred to by the term "diaper(s)".

Definition: Humans must consciously relax the external sphincter muscles to expel waste. The urethral and sphincter muscles are closely linked, and experiments by Dr. Harrison Weed at the Ohio State University Medical Center have shown that they can only be contracted together, not individually, and that they both show relaxation during urination. This explains why defecation is always accompanied with urination, which further leads to the conclusion that a diaper cannot be soiled without being wet too. So, in order to determine if a diaper needs to be changed, one only needs to check if it is wet. Therefore, excretions in general will be referred to hereinafter by the term "urination".

Prior Art Relating to Wetness Detection

One aspect of this invention relates to detection of wetness in diapers. Many of the prior art solutions are based on detecting changes in conductivity between two conductors, typically positioned in the diaper. Examples are disclosed in U.S. Pat. No. 4,106,001 U.S. Pat. No. 4,205,672 U.S. Pat. No. 4,356,818 U.S. Pat. No. 4,484,573 U.S. Pat. No. 4,539,559 U.S. Pat. No. 4,653,491 U.S. Pat. No. 4,704,108 U.S. Pat. No. 4,738,260 U.S. Pat. No. 4,754,264 U.S. Pat. No. 4,768,023 U.S. Pat. No. 4,796,014 U.S. Pat. No. 4,800,370 U.S. Pat. No. 5,036,859 U.S. Pat. No. 5,264,830 U.S. Pat. No. 5,266,928 U.S. Pat. No. 5,341,127 U.S. Pat. No. 5,392,032 U.S. Pat. No. 5,395,358 U.S. Pat. No. 5,469,145 U.S. Pat. No. 5,469,146 U.S. Pat. No. 5,568,128 U.S. Pat. No. 5,570,082 U.S. Pat. No. 5,760,694 U.S. Pat. No. 5,790,036 U.S. Pat. No. 5,796,345 U.S. Pat. No. 5,838,240 U.S. Pat. No. 5,868,723 U.S. Pat. No. 5,902,296 U.S. Pat. No. 5,903,222 U.S. Pat. No. 6,097,297 U.S. Pat. No. 6,163,262 U.S. Pat. No. 6,200,250 U.S. Pat. No. 5,908,411 U.S. Pat. No. 5,959,535 U.S. Pat. No. 6,091,336 U.S. Pat. No. 6,097,297 U.S. Pat. No. 6,163,262 U.S. Pat. No. 6,200,250 U.S. Pat. No. 6,373,395 U.S. Pat. No. 6,384,728 U.S. Pat. No. 6,559,772 U.S. Pat. No. 6,580,013 U.S. Pat. No. 6,583,722 U.S. Pat. No. 6,603,403 U.S. Pat. No. 6,756,521 U.S. Pat. No. 6,916,968 U.S. Pat. No. 7,145,053 U.S. Pat. No. 7,250,547 US 2005/0195085 US 2006/0258916 and WO/2008/079296.

Several solutions suggest conductors that are built into the diaper during manufacture, and then connected to a device attached to the diaper. Such diapers can be relatively expensive.

Still other solutions suggest disposable conductors for use with commercially available diapers. These solutions are complicated to use, uncomfortable to the wearer, expensive, and wasteful.

Prior Art Relating to Toilet Training

Another aspect of this invention relates to toilet training. A parent would like to know exactly when the toddler needs to relieve himself, and assist him in doing it right. In this manner, the child will learn quickly to associate the act of urination with the need to go to the toilet. As a result, the child becomes toilet trained within a short time.

Examples of prior art for electronic alarm devices for toilet training are disclosed in U.S. Pat. No. 5,537,695 U.S. Pat. No. 5,560,051 U.S. Pat. No. 5,703,567 and U.S. Pat. No. 5,817,076.

Prior art solutions were unsatisfactory. Some offer alarm systems based on a potty chair. However, in order for the alarm to operate, the toddler has to be already seated in that chair. Others suggest modifications in the diaper or usage of some special article of clothing.

Prior Art Relating to Bedwetting

Still another aspect of this invention relates to bedwetting. A bedwetting child controls his bladder while awake, but unfortunately can not do so while being asleep. The best way to treat bedwetting is by behavioral conditioning, by which the child learns to associate the alert with the physical sensations of urination. A system wakes up the child once urination starts.

Examples of prior art for electronic alarm devices for bedwetting are disclosed in U.S. Pat. No. 4,191,950 U.S. Pat. No. 4,212,295 U.S. Pat. No. 4,347,503 U.S. Pat. No. 4,271,406 U.S. Pat. No. 4,356,479 U.S. Pat. No. 4,640,276 U.S. Pat. No. 4,760,383 U.S. Pat. No. 4,977,906 U.S. Pat. No. 5,043,704 U.S. Pat. No. 5,074,317 U.S. Pat. No. 5,144,284 U.S. Pat. No. 5,291,181 U.S. Pat. No. 5,459,452 U.S. Pat. No. 5,537,095 U.S. Pat. No. 5,845,644 U.S. Pat. No. 6,072,384 U.S. Pat. No. 5,341,127 U.S. Pat. No. 6,292,102 U.S. Pat. No. 6,774,800 U.S. Pat. No. 7,053,781 U.S. Pat. No. 7,151,458, U.S. Pat. No. 7,209,044 and the product DRI Sleeper®.

Some prior art solutions for bedwetting suggest placing a sensing device near the user's crotch area, and connecting it by wires to an alarming device positioned near his head. These solutions cause discomfort to the wearer, and even may strangle him. The DRI Sleeper product suggests a sensor unit and an alarm unit, wirelessly connected. The user is instructed to put the sensor unit inside an absorbing pad, and put the pad into the child's underpants. This solution requires preparations and disposables. The sensor unit is large, uncomfortable to the wearer, gets soiled every time it is used, and needs to be cleaned.

Prior Art Relating to SIDS Alarms

Still another aspect of this invention relates to monitoring of breathing.

A baby's life could be saved if SIDS (Sudden Infant Death Syndrome) would be indicated, by recognizing he stopped breathing.

If the indication arrives early enough, it may be possible to restart breathing, by mild stimulation of the baby's nervous system by patting his skin or by rubbing his back or feet. If indication arrives within a few minutes, it may still be possible to save the baby by artificial respiration.

A similar situation, which also requires immediate alert, is the breathing cessation of old or sick people.

The prior art suggests many solutions for this purpose, such as in U.S. Pat. No. 5,774,055 U.S. Pat. No. 5,825,293 U.S. Pat. No. 5,864,291 U.S. Pat. No. 5,928,157 U.S. Pat. No.

5,993,397 U.S. Pat. No. 6,267,730 US 2001/0026222 US 2005/0053262 US 2005/0277842 US 2006/0206035 US 2006/0258916 US 2007/0076935 and US 2007/0149883.

Some prior art solutions (such as BabySense©, Nanny© and AngelCare© among others) monitor the breathing movements by flat sensor pads installed under the mattress. These require installation to a bed, are expensive, provide protection only when the baby sleeps in that specific bed, and are not effective when two or more babies share the same bed.

US 2006/0258916 offers a system with a pressure sensor built into a clip, which hangs it to the diaper's edge. This is unreliable and unsafe, as the device may be relocated by the baby movements, or may be detached by the baby.

Prior Art Relating to Attachment Arrangements

Hereinbefore, prior art of personal monitoring devices have been discussed in general. However, the issue of securely attaching a device to a person requires further discussion.

Referring specifically to U.S. Pat. No. 4,484,573, an alarming device is simply positioned within the baby's panties, with no attachment at all. Obviously this solution is unsafe as the baby may just pull it off. It might be soiled, and taking it into baby's mouth is unhealthy. Moreover, the baby might even swallow it.

Referring specifically to U.S. Pat. No. 4,205,672, a pair of jaw members is closed (by means of a spring force) on the upper edge of the diaper, a location which is very far from the expected wet region. The device hangs onto the diaper by means of friction, so it might be pulled off unintentionally.

Referring specifically to U.S. Pat. No. 4,796,014 a special safety pin is suggested for attaching a device to the outside of the diaper, and for extending two conductors into the diaper. This solution is very unsafe. Pulling the device strong enough will bend the pin, thus causing the sharp tip to be released and hurt the baby.

U.S. Pat. No. 5,392,032 suggests a diaper-cover having snaps, to which a device is attached by another set of snaps. Obviously, snaps can be detached just as easily as they are attached. The baby can just pull the device off the diaper-cover, rendering it useless and even dangerous. Moreover, such a cover cannot be used with water-proof diapers.

U.S. Pat. No. 5,568,128 suggests a tensile band, shaped as a clip, connected to a housing. The device is attached to the upper edge of a diaper. A pair of spikes, mounted on the band, poke through the diaper (from inside out), and two sockets in the housing accept them. The device is detached from the diaper by pulling it by the application of a force, which is strong enough to part the spikes from the sockets. This is clearly evident from the following quote, taken from said patent: "The tensile band is designed such that the spikes and the sockets are together, and it takes force to part them". This solution lacks a safety mechanism to prevent accidental detachment. It is also obvious that the device can only be located at the upper edge of the diaper, very far from the expected wet region.

US 2006/0258916 suggests attaching a monitoring system to a diaper by means of a belt clip. The clip can be pulled off by the baby, or be misplaced by the baby's movements.

In conclusion, the prior art solutions which have been proposed so far are unsafe, unreliable, expensive to manufacture, uncomfortable to wear, too complicated to operate, require expertise for maintenance, or require modifications to the diaper manufacturing process, thereby increasing the diaper cost.

More specifically, the prior art solutions fail to suggest an easy to operate, quick and secure arrangement for attaching a monitoring device to a diaper, yet preventing unintentional detachment.

Objects of the Present Invention

It is therefore an object of the present invention to provide secure attachment mechanisms for attaching monitoring devices to diapers.

It is still another object of the present invention to provide such attachment mechanisms which can operate with various types of diapers.

It is still another object of the present invention to provide such attachment mechanisms which can attach various types of monitoring devices.

It is still an object of the present invention to provide such attachment mechanisms, portions of which can also serve as probes for sensing wetness within the diaper.

Other objects and advantages of this invention will become apparent as the description proceeds.

SUMMARY OF THE INVENTION

The present invention relates to a device for monitoring the condition of a person, which comprises: (a) a casing; (b) electronic circuitry; and (c) at least one secure attachment mechanism, each comprising a first member which is capable of moving in a forward direction up to a locking state, at which it is interlocked by at least one second member, so that said first member cannot be moved backward by applying a first backward force, unless said interlock is unlocked, by applying at least one second force, independent of said first force.

Preferably, said first member is a spike having at least one recess, and wherein at said locking state said second member is introduced into said recess, thereby preventing said spike from moving backward. Preferably, said spike is used, among other functions which will be described hereinafter, for activating a switch, which is part of said electronic circuitry.

In one embodiment of the invention: (a) said second member is a socket member having a flat surface with an opening which is large enough for said spike to pass though; (b) said socket member is capable of moving so that its flat surface coincides with a virtual plane which is perpendicular to said forward direction; (c) said socket member, when at rest is so positioned, by means of an elastic member that applies to it a biasing force, to enable a tip of said spike to enter through said opening while said spike moves forward, and wherein said socket member prevents backward movement of said spike at the locking state; (d) said spike is positioned such that during moving forward, a diagonal portion of said spike gradually pushes said socket member against said biasing force, up to said locking state, at which said biasing force pushes the socket member into said recess; (e) an edge of said recess, facing said socket member at said locking state, is substantially perpendicular to said backward direction; and (f) said second force is required for retracting said socket member out of said recess, against said biasing force.

In another embodiment of the invention: (a) said second member is a flat elastic socket member in which there is an elongated opening, shaped such that it forms at least one spring member; (b) the width of said opening, at a point designated for said spike to enter, is smaller than the width of said recess; (c) said socket member is affixed at one of its ends to said casing; (d) said spike is positioned so that during moving forward and entering said opening, said spike gradually bends said spring member, thus causing the opening to gradually increase, up to said locking state, at which the spring member is introduced into said recess; and (e) said second force is required for further bending said socket member until said opening is large enough to enable release of said spike.

In still another embodiment of the invention: (a) said second member is an elastic member having a first end affixed to said casing, and a moveable end, wherein moving the moveable end in a plane perpendicular to the forward direction requires overcoming an elasticity force of said elastic member; (b) said spike is positioned such that during moving forward, a diagonal portion of said spike gradually applies force to said elastic member, causing its movable end to move perpendicularly with respect to said forward movement, up to said locking state, at which said elastic member is introduced into said recess by said elasticity force; (c) an edge of said recess, facing said elastic member at said locking state, is substantially perpendicular to said backward direction; and (d) said second force is required for retracting said elastic member out of said recess, against said elasticity force.

In still another embodiment of the invention: (a) said first member is a spike having a bulge close to its tip; (b) said second member has a form of a flat socket member having an opening for receiving said spike; (c) said bulge and said opening are so shaped that said bulge can pass through said opening only when both shapes are aligned; (d) said spike is positioned such that in said locking state said bulge is past the opening, but so that said shapes are misaligned; and (e) said second force is required for turning said spike until said bulge is realigned with said opening.

In an embodiment of the invention, the device comprises two secure attachment mechanisms, wherein said spikes are connected by a bridge member.

In still another embodiment of the invention: said spikes are connected by an elastic bridge member at a certain distance apart one from the other; (b) portions of said recesses face opposite directions; (c) said second members have a form of a flat socket member, having at least one opening for receiving a corresponding spike; (d) said socket members are positioned within said casing, such that the distance between the outer edges of said openings is smaller than the distance between the outer edges of said spikes; (e) said spikes are positioned such that during moving forward, a diagonal portion of at least one spike is gradually pressed toward the center of its corresponding opening, thus gradually bending said elastic bridge member, up to said locking state at which the edge of said opening is introduced into said recess by the elasticity force of said bridge member; (f) an edge of said recess which faces said socket member at said locking state is substantially perpendicular to said backward direction; and (g) said second force is required for retracting said spikes until the edges of said openings are no longer positioned within said spikes recesses.

In an embodiment of the invention, said electronic circuitry comprises: (a) at least one sensing circuitry, each measuring at least one value relating to a corresponding characteristic of said person's condition, and issuing at least one signal indicative of said measurement; (b) at least one alarming circuitry for activating alarm means; and (c) control circuitry for accepting said signal and for activating said alarm means, if said measured value is not within a selectable range. Preferably, said characteristic of condition is selected from the group comprising: breathing; body temperature; heartbeat; motion; wetness; whereabouts; environmental temperature; and sound pressure in said person's surroundings.

In an embodiment of the invention, said spike has at least one conductive area on its external surface.

In an embodiment of the invention, said sensing of motion is used for detecting breathing movements of said person's body. In an embodiment of the invention, said sensing of motion is performed by at least one means selected from the group comprising: anisotropic magnetoresistive (AMR) sensors, giant magnetoresistive (GMR) sensors, displacement sensors, tilt sensors, Hall-effect sensors, gyro sensors, angular rate sensors and photosensitive sensors.

In an embodiment of the invention, said alarm means is at east one means selected from the group comprising: audible alarms, visual alarms, vibrating alarms and radio transmission.

The invention also relates to a system which comprises a local device of one of the embodiments described so far, and at least one remote device, wherein said devices are wirelessly connected. Preferably, said devices perform a PARI procedure.

In an embodiment of the invention, said system is used for locating a lost person.

In an embodiment of the invention, said device is used for detecting breathing movements of said person's body, and wherein said vibrating alarm is used for stimulating said person's nervous system to restart breathing.

In an embodiment of the invention, said monitoring device and said remote device exchange information taking at least one form selected from the group of audio, video and numerical data.

BRIEF DESCRIPTION OF THE DRAWINGS

The present invention will be better understood and further advantages will become apparent when referring to the drawings listed hereunder and the following detailed description of the invention.

The drawings show some embodiments of the invention by ways of illustration. It is to be understood that other embodiments may be utilized, and structural, electrical, as well as procedural changes may be made without departing from the scope of the present invention.

DETAILED DESCRIPTION OF PREFERRED EMBODIMENTS

The present invention relates to monitoring devices which are securely attachable to diapers.

Several preferred embodiments of secure attachment mechanisms are disclosed hereinafter.

Still other preferred embodiments of the monitoring device, having various functionalities, are also disclosed hereinafter.

Still other preferred embodiments of this invention may take the form of systems comprising distinct devices connected wirelessly.

In still other preferred embodiments, said systems may comprise bidirectional communication channels between the person being monitored and a caregiver.

Secure Attachment Mechanisms

The monitoring device of the present invention may be detached from one diaper, and re-attached to another. Its Secure Attachment Mechanism ensures that detachment can be performed only intentionally, by someone skilled enough.

Definition: "Secure Attachment Mechanism" is defined as a mechanical arrangement in which a first member is capable of moving forward up to a locking state, in which it is interlocked by at least one second member, so that said first member cannot be moved backward by applying a first backward force, unless said interlock is unlocked, by applying at least one second force, independent of said first force.

Several embodiments of Secure Attachment Mechanisms will be disclosed.

Sliding Socket Embodiment

FIGS. 1 to 4C illustrate a first preferred embodiment of a Secure Attachment Mechanism, hereby referred to as the "Sliding Socket Embodiment", which discloses the best mode contemplated by the inventor, of carrying out the invention.

Figure 1:
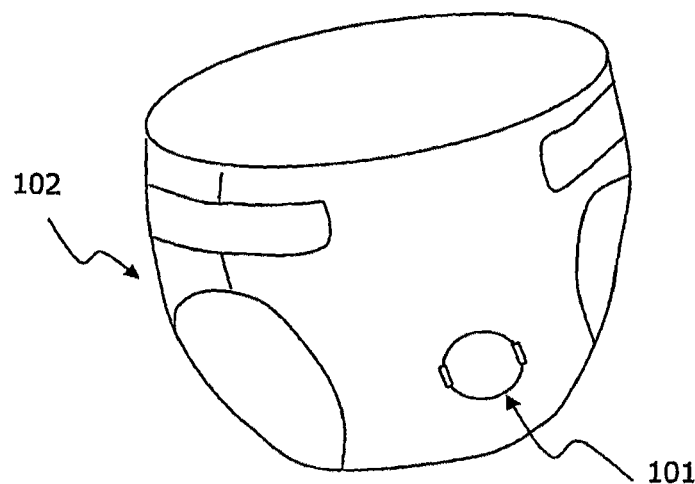
FIG. 1 shows a monitoring device attached to a diaper.
Figure 2A:
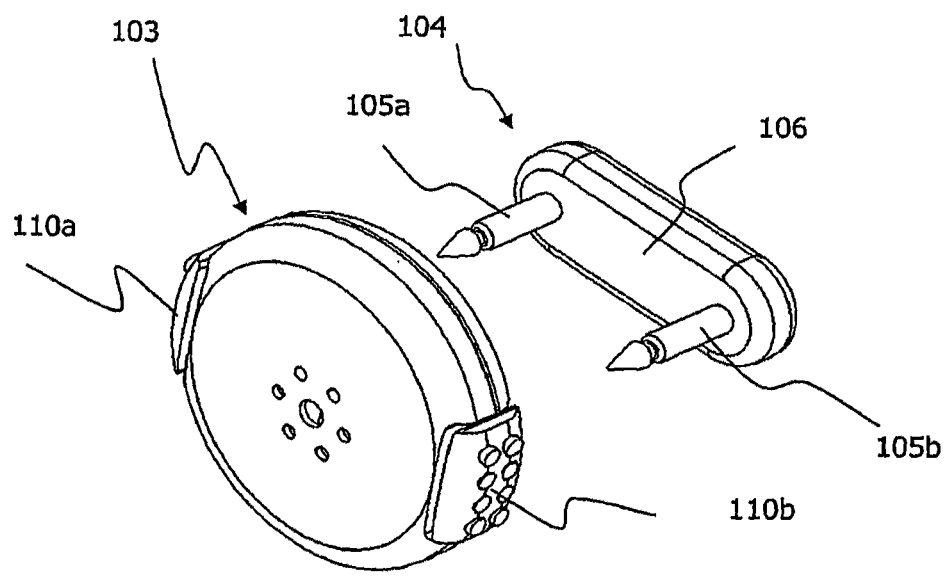
FIGS. 2A and 2B show perspective views of the monitoring device.
Figure 2B:
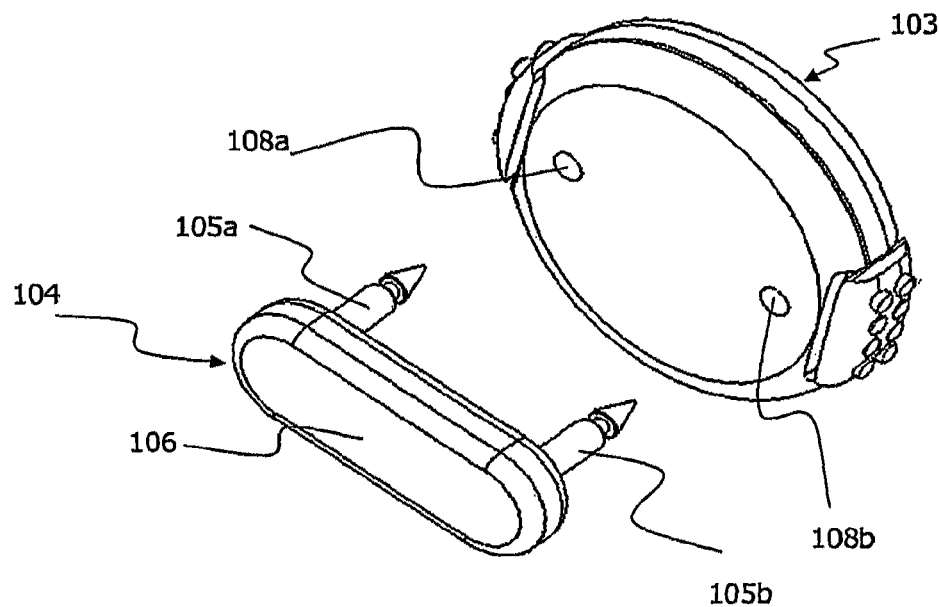
Figure 3:
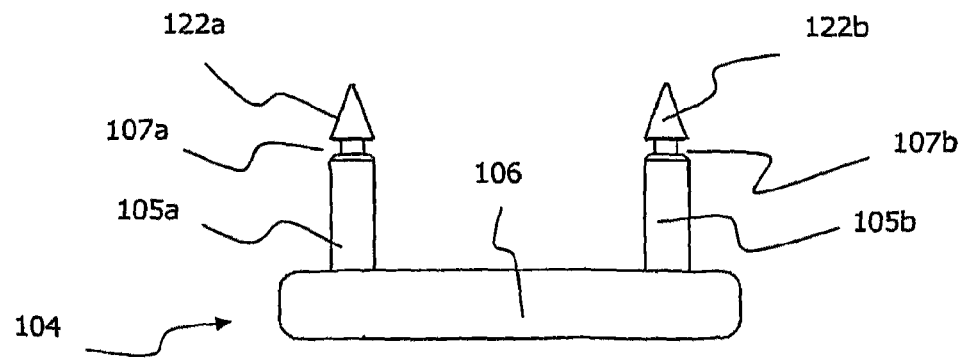
FIG. 3 shows a side view of the locker with its components.

FIG. 1 shows a monitoring device 101 attached to a diaper 102. The device comprises a casing 103 and a locker 104. The locker comprises two spikes (105a, 105b respectively), and a bridge 106, rigidly connecting said spikes. Each spike has a recess (107a, 107b respectively).

The casing 103 has two holes (108a, 108b respectively—FIG. 2B) for accepting said two spikes. The device 101 further comprises two socket members (109a, 109b respectively—FIGS. 4A and 4B) within the interior of casing 103, each socket member is attached to a releasing pad (110a, 110b respectively). The pads extend on the sides of the casing.

Each socket member has an opening 111 formed by two partially overlapping holes (111a, 111b respectively). The larger hole 111a is large enough for the spike to pass through, while the smaller hole 111b has a diameter slightly larger than the diameter of the recess (107a, 107b respectively), yet smaller than the outer diameter of the spike.

The socket members (109a, 109b) are positioned inside the casing so that their flat surfaces (129a, 129b) share a single plane, their pads (110a, 110b) face opposite directions, and all the holes share a same line of symmetry. They are allowed to move along said line.

Definition: Throughout this application, the term "forward" refers to the direction, relative to the casing, in which a spike moves closer to the casing in order to become interlocked, and the term "backward" refers to the opposite direction.

Figure 4A:
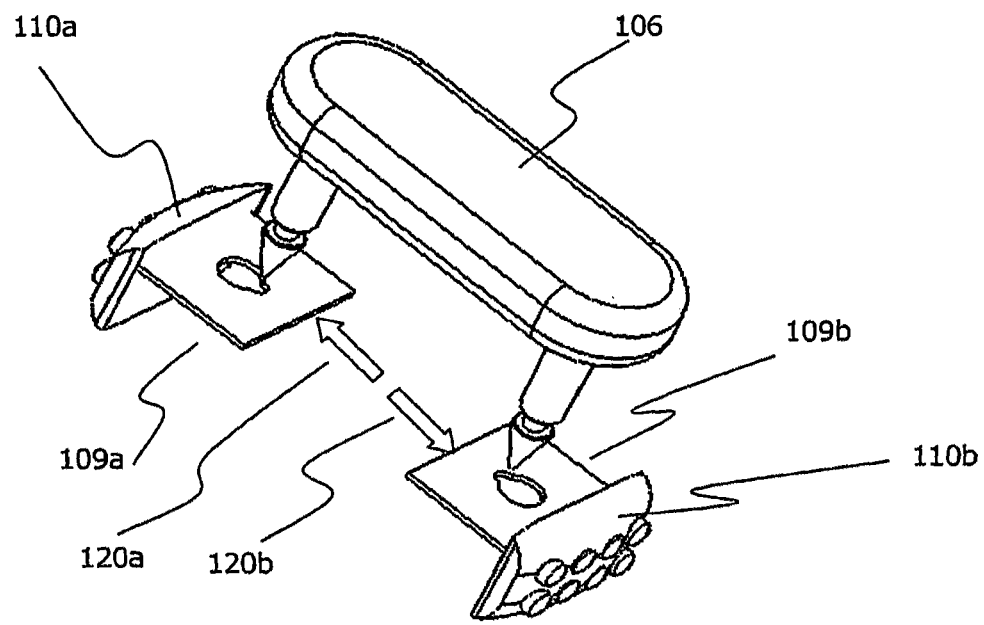
FIGS. 4A to 4C show perspective views of the "Sliding Sockets Embodiment"
Figure 4B:
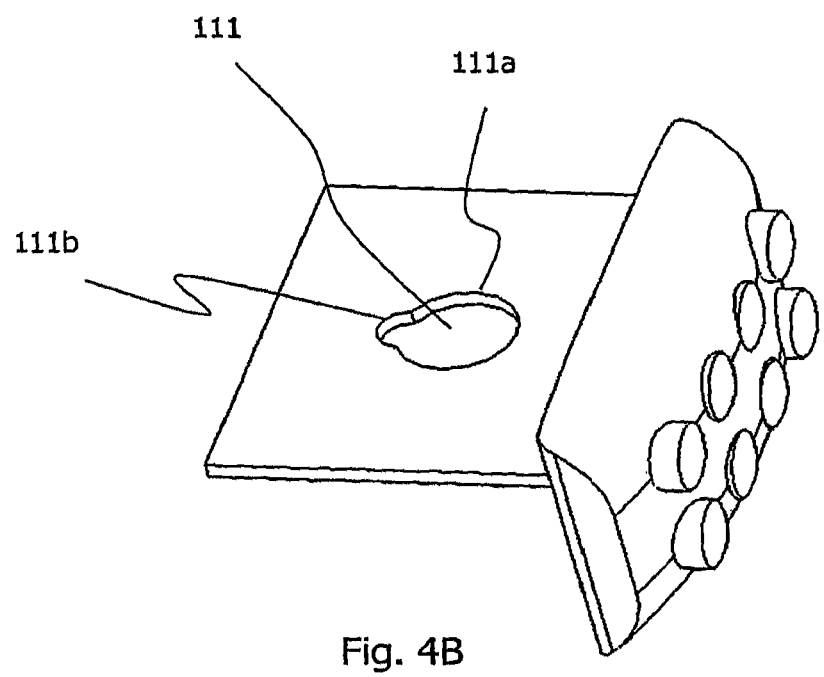
Figure 4C:
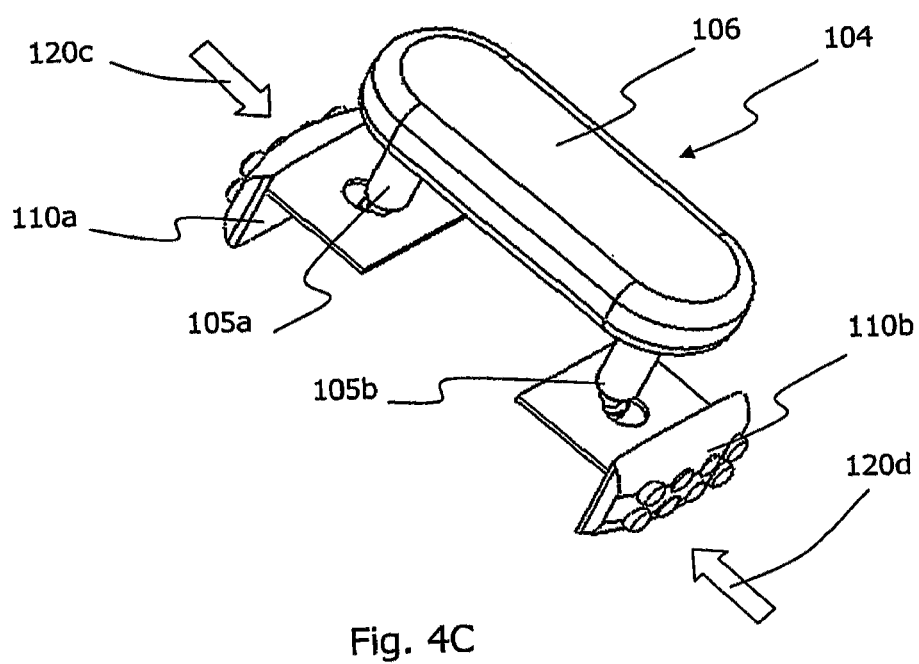

The socket members are also under constant force(s), applied by one or more internal elastic elements, pushing them outward, in the directions of arrows (120a, 120b—FIG. 4A).

At rest, the center of the smaller portion 111b of each opening is aligned with the central axis of the corresponding casing hole (108a, 108b).

Upon attachment, the spikes (105a, 105b) are pressed forward, against the inner side of the diaper, until they poke outside, then inserted into the casing holes (108a, 108b), thus the axis of each spike is aligned with the center of a corresponding smaller hole (111b).

As each spike continues to move forward, the surface of its tip (122a, 122b respectively) pushes the corresponding socket member inward, thus pressing said elastic elements. Eventually the spike passes through the larger hole.

When the recesses (107a, 107b) are aligned with the socket members (109a, 109b), the now compressed elastic elements push the socket members into said recesses.

In this locking state, the spikes (105a, 105b) are prevented from moving backward. The attachment is secured, and the diaper is ready to be worn.

The interlocking by the structure is very secure. In order to release the spikes from the casing, the user must realign the larger portions of the openings 111a with the spikes. This requires simultaneous application of two releasing forces (illustrated by arrows 120c, 120d shown in FIG. 4C), to move the pads (110a, 110b respectively) inward. Only then the user can pull the spikes backward, by the application of still another force on the spikes (generally on bridge 106).

It should be noted that before reaching the locking state, the forward movement of each spike was able to cause an inward movement of its socket only because the tip surfaces (122a, 122b) of the spikes are diagonal (i.e. not perpendicular) with respect to the forward direction, and this diagonal relation allows generation of a sub-vector of the forward force in the inward direction. On the other hand, the recess edge, that faces the backward direction, is indeed perpendicular to the backward direction. Pulling the spike backward (after the locking state had been reached) will not create any sub-vector in the inward direction, due to the perpendicularity of these directions. Practically however, even when said edge is not exactly perpendicular (i.e. almost perpendicular to the backward direction), the sub-vector force will not be sufficient to move the socket member inward, due to friction forces.

It should also be noted that the releasing forces (120c, 120d) must be independent of the backward force, since they cannot be derived as sub-vectors of the backward force, as discussed above.

This arrangement conforms to the Secure Attachment Mechanism definition as was stated above. More specifically, for each spike-socket arrangement, the spike corresponds to the first member, and the socket member corresponds to the second member of said definition.

This Secure Attachment Mechanism ensures that the device cannot be detached from the diaper unintentionally. No doubt that such a complicated detachment operation cannot be made by the baby who wears the diaper.

Generalized Sliding Sockets Embodiment

FIGS. 5A to 5E illustrate another embodiment of a Secure Attachment Mechanism, hereby referred to as the "Generalized Sliding Socket Embodiment". It is a generalized version of the previous embodiment.

This embodiment, too, utilizes spikes 205 and sliding socket members 209, and operates in a manner similar to the embodiment shown above.

However, this embodiment shows that the geometry of the cross section of the spike 205 and the geometry of the opening 211 in the socket member 209 do not matter at all, as long as the opening 211 is large enough to enable the spike 205 to move forward through it, until the spike recess 207 is aligned with the socket member 209.

For illustration purposes, FIGS. 5A to 5D intentionally show a spike with a rectangular shaped cross section and a socket member with a round opening.

Upon alignment, the now compressed elastic element (not shown) pushes the socket member 209 toward the recess, so the edge of the opening 211 moves into the recess 207, thus preventing the spike from moving backward.

In this embodiment, too, detachment can only be obtained by simultaneously pressing both pads 210 by two forces independent from the backward force.

This ensures that the device cannot be detached unintentionally or by chance. No doubt that detachment cannot be made by the baby who wears the diaper.

This structure, too, conforms to the Secure Attachment Mechanism definition as was stated above.

Figure 5A:
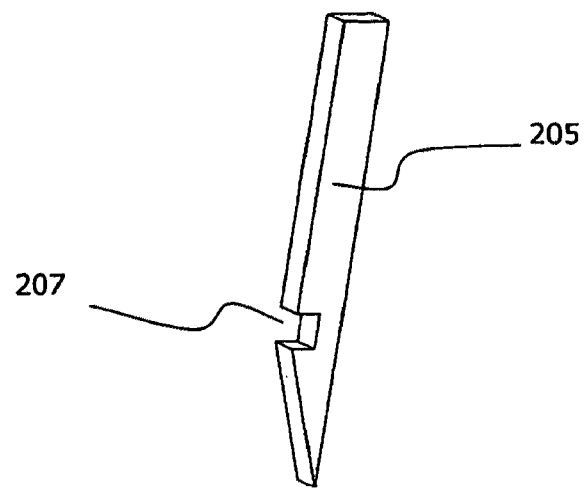
FIGS. 5A to 5E show perspective views of the "Generalized Sliding Sockets Embodiment"
Figure 5B:
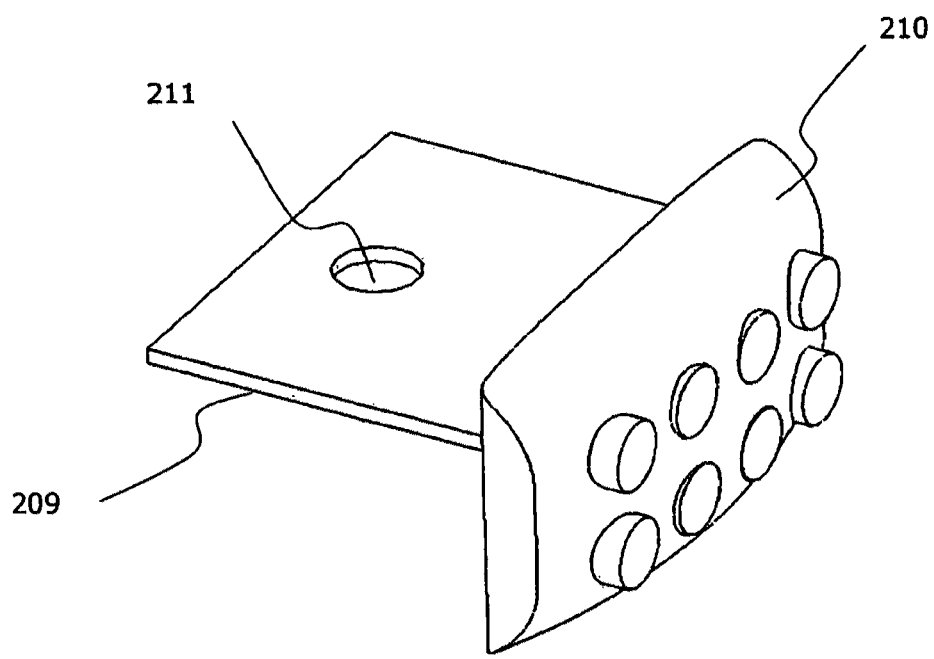
Figure 5C:
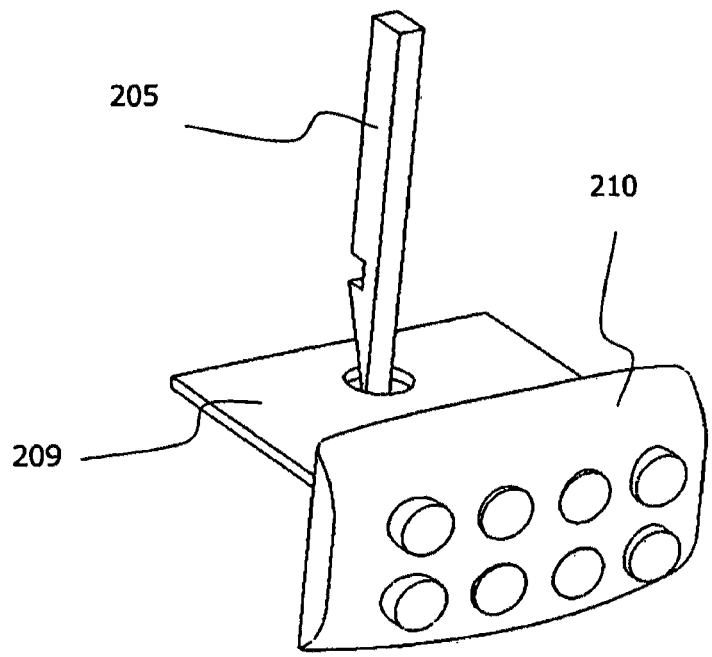
Figure 5D:
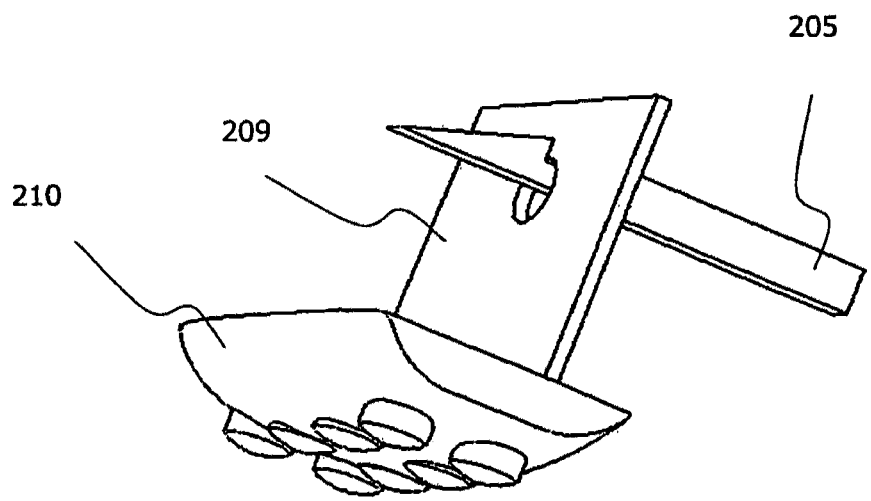
Figure 5E:
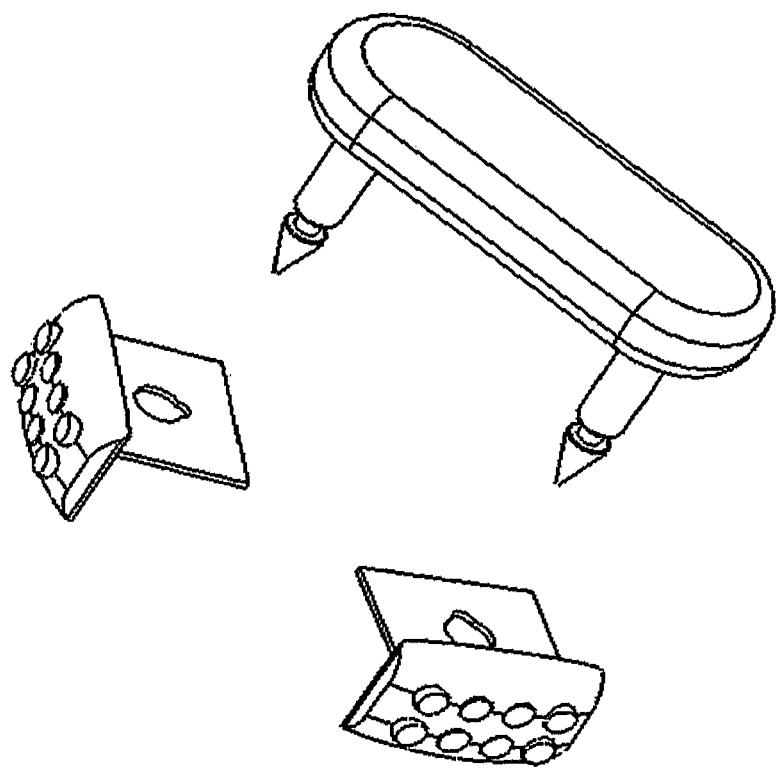

It is readily apparent that alternate embodiments, in which the pads of the socket members do not face opposite directions, are also feasible, as demonstrated in FIG. 5E. All such embodiments are considered to be equivalent to the Generalized Sliding Socket Embodiment presented above and fall within the spirit and the scope of this invention.

Bent Sockets Embodiment

FIGS. 6A to 6E illustrate still another embodiment of a Secure Attachment Mechanism, hereby referred to as the "Bent Sockets Embodiment".

Figure 6A:
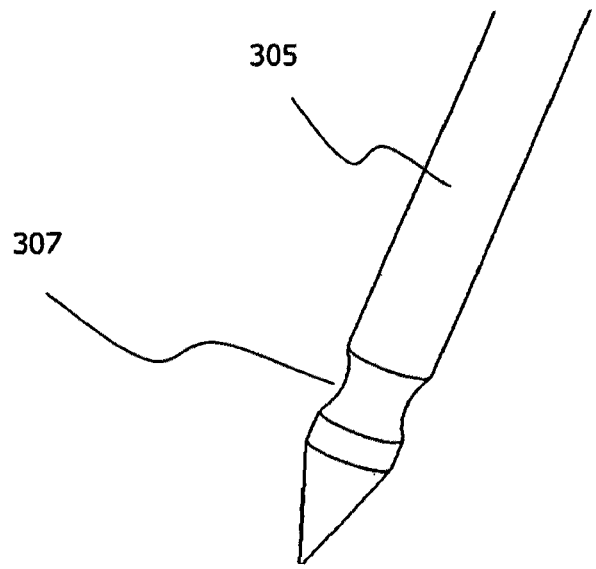
FIGS. 6A to 6G show perspective views of the "Bent Springs Embodiment" and variations thereof.
Figure 6B:
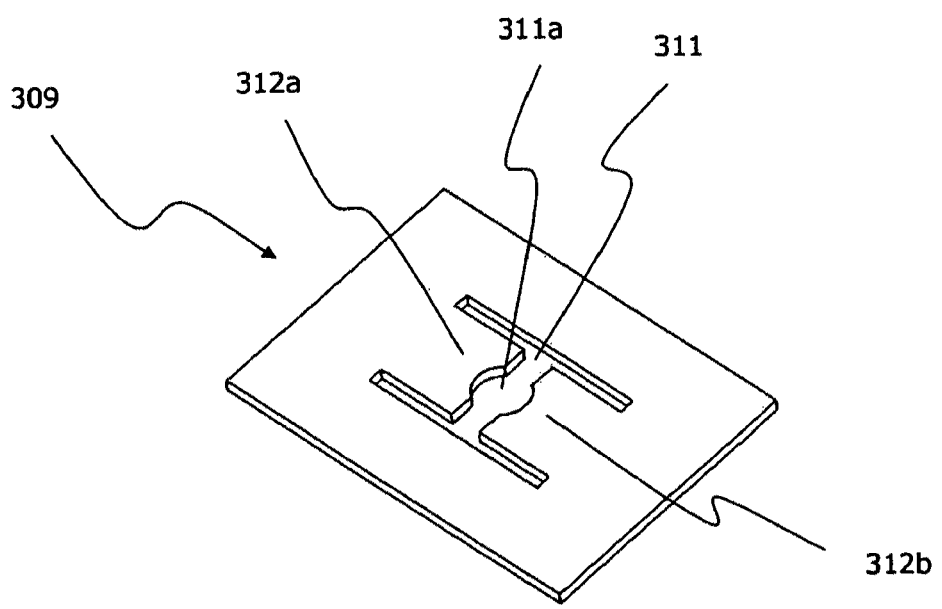
Figure 6C:
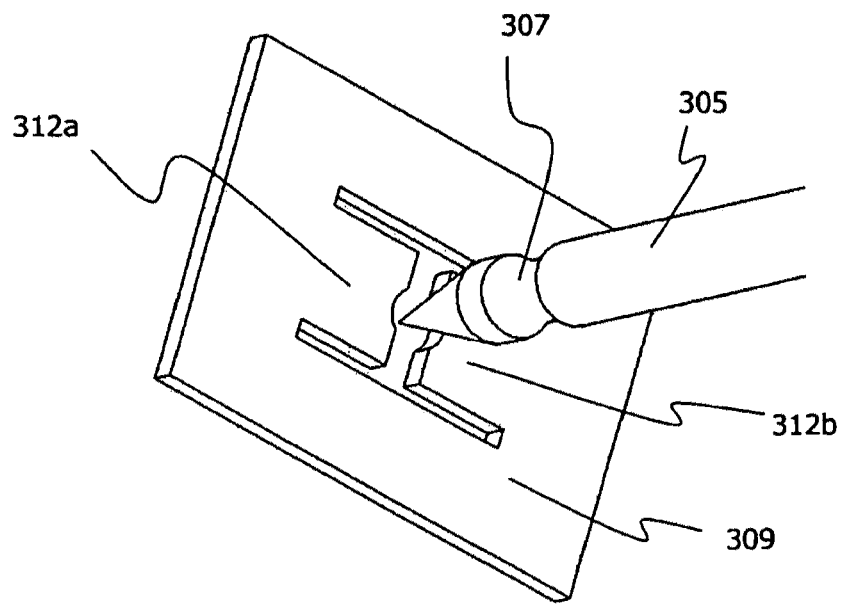

The spike 305 has a recess 307. The socket member 309 has a flat configuration and is made of elastic material. The socket member 309 further has an H-like opening 311 as shown in FIG. 6B. At the center of the opening 311, there is a round hole 311a, having a diameter smaller than the diameter of said recess 307.

When the spike is pushed forward into the hole 311a, it pushes the spring members (312a, 312b) forward and aside, thus enlarging the opening between them.

Figure 6D:
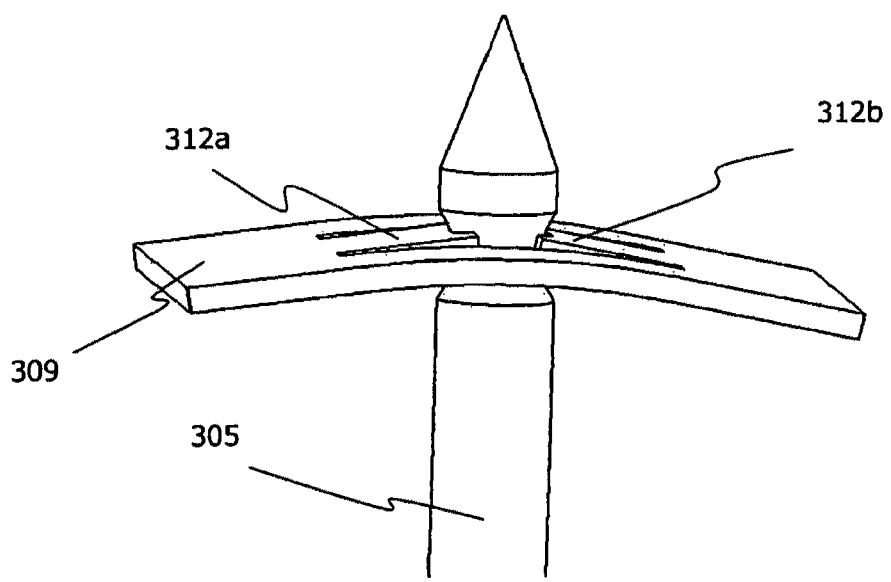

Upon alignment between the recess 307 and the spring members (312a, 312b), the spring members move into said recess. At this state, the spring members are still bent, as shown in FIG. 6D, since the opening 311a is smaller than the diameter of the recess.

In this locking state, pulling of the spike 305 backward only makes the spring members 312a, 312b grip the spike even stronger. As evident, in this embodiment the recess does not have to be neither perpendicular to the spike axis nor sharp.

Figure 6E:
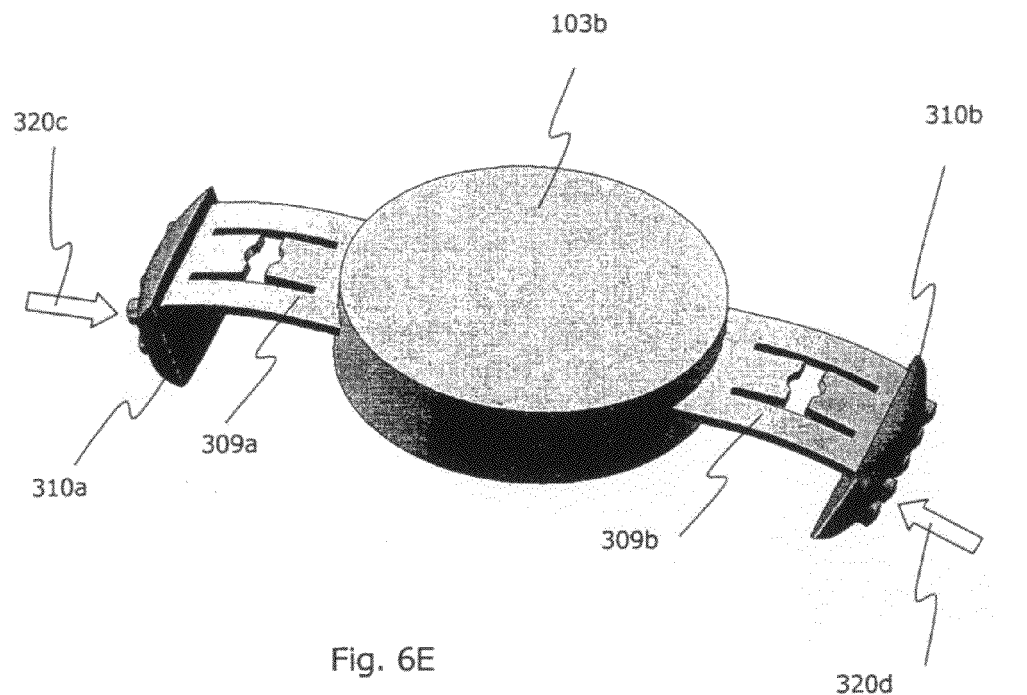

One way to release the spikes is to bend the socket members (309a, 309b) further, thus enlarging the openings 311. This can be achieved by applying two simultaneous bending forces on the socket pads (illustrated by arrows 320c, 320d shown in FIG. 6E), while providing support at the opposite end of each socket member. FIG. 6E shows a schematic body 103b being a part of casing 103, which provides such a support. Both socket members (309a, 309b) are affixed at one end to said body 103b, and at their opposing end to a pad 310a, 310b respectively. The simultaneous application of two forces (320c, 320d) on the pads (310a, 310b) causes bending of both socket members (309a, 309b), thus enlarging their openings. Only then the spikes can be pulled backward.

This structure, too, conforms to the definition of the Secure Attachment Mechanism as was stated above.

Obviously, this complex combination of forces (320c, 320d) acting simultaneously on the two pads on one hand, and applying, still another simultaneous pulling force on the spikes on the other hand, must be made intentionally by a skilled user, and can never be accomplished by a baby or just happen by chance.

Figure 6F:
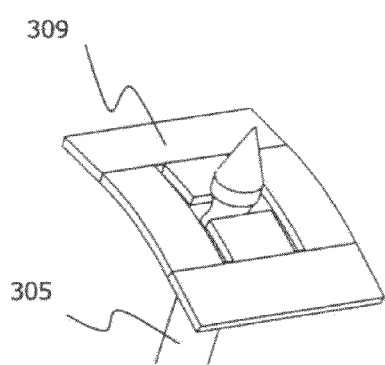
Figure 6G:
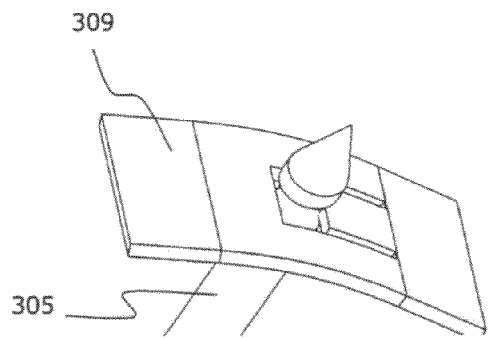

It is readily apparent that an embodiment that uses a similar structure but omitting said hole (311a) is also feasible, as shown in FIG. 6F. It is also apparent that an embodiment that uses an opening with only one spring member is also feasible, as shown in FIG. 6G. All such embodiments are considered to be equivalent to the Bent Sockets Embodiment presented above and fall within the spirit and the scope of this invention.

Flexible Leaves Embodiment

FIGS. 7A to 7D illustrate another embodiment of a Secure Attachment Mechanism, hereby referred to as the "Flexible Leaves Embodiment".

Figure 7A:
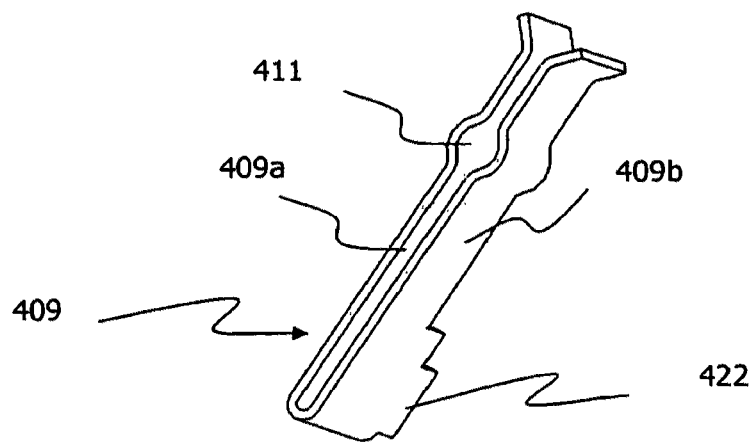
FIGS. 7A to 7D show perspective views of the "Flexible Leaves Embodiment"
Figure 7B:
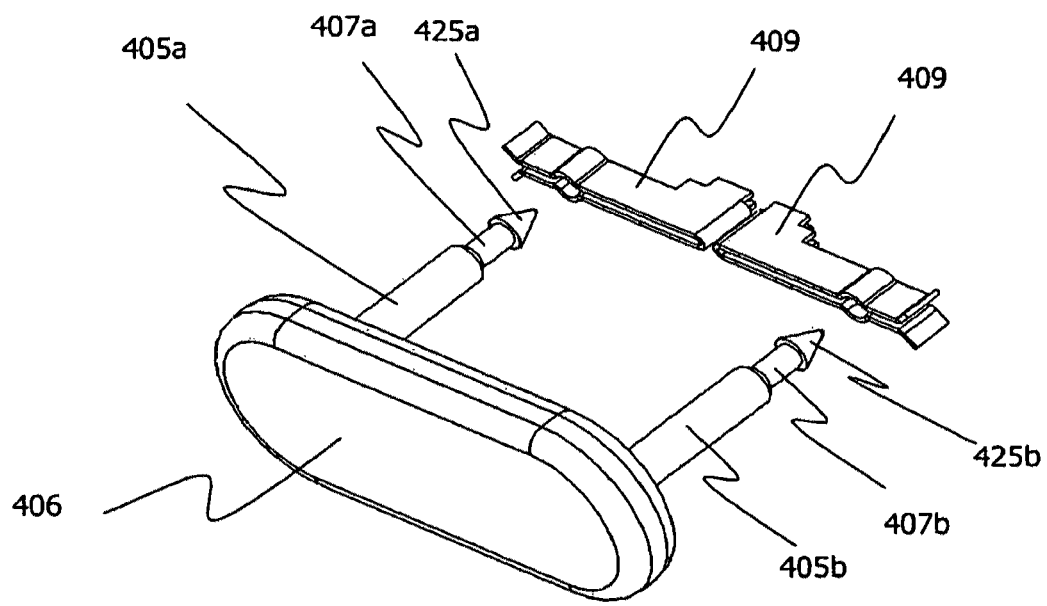

FIG. 7A shows a socket member 409 having two flexible leaves (409a, 409b). The base of the socket member 422 is affixed to the casing 103.

Figure 7C:
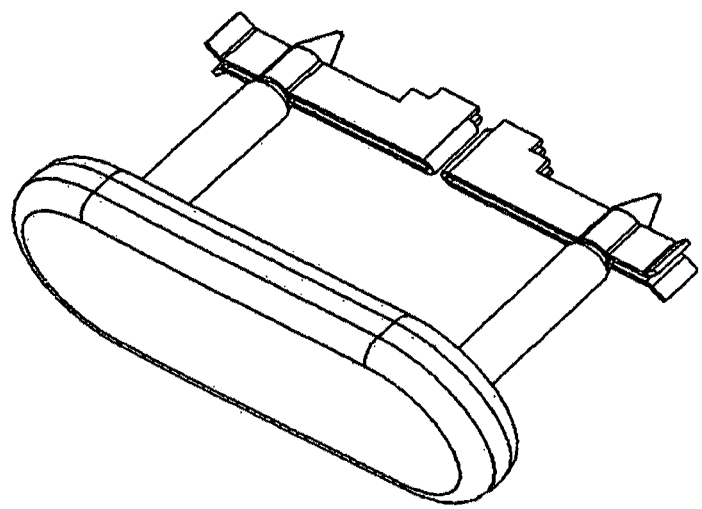

The diagonal tip (425a, 425b respectively) of the spike (405a, 405b, respectively) enters the round opening 411 between the leaves, gradually spreading the leaves apart, until the recess 407 of the spike is aligned with the leaves (409a, 409b). The leaves then move into the recess, thus locking and preventing it from moving backward (FIG. 7C).

In order to release the spike, the leaves (409a, 409b) must be moved out of the recess.

Figure 7D:
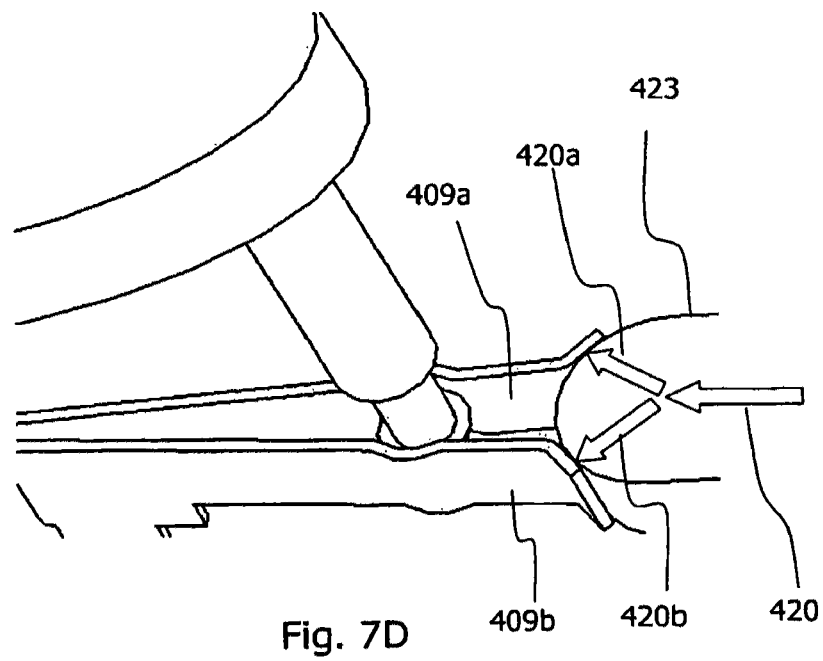

FIG. 7D shows a key member 423, being pressed by a force, as indicated by arrow 420, which produces two sub-vectors (420a, 420b) acting on the leaves (409a, 409b), causing the leaves to depart and retract from the recess.

This structure, too, conforms to the definition of the Secure Attachment Mechanism as was stated above.

Once again, such a simultaneous combination of three forces, two forces pressing the key members (423) inward and one force pulling the locker (with the two spikes) backward, must be made intentionally and by a skilled user, and can never be accomplished by a baby or just happen by chance.

It is readily apparent that an embodiment that uses a similar structure but omitting said hole (411) is also feasible. It is also apparent that an embodiment that uses a socket member having only one leaf is also feasible. It is also apparent that still another embodiment wherein the socket member is a non-elastic member pivotally connected to said casing at one end, and biased towards the spike at its other end, is also feasible. All such embodiments are considered to be equivalent to the Flexible Leaves Embodiment presented above and fall within the spirit and the scope of this invention.

Separate Spikes Embodiment

Figure 8:
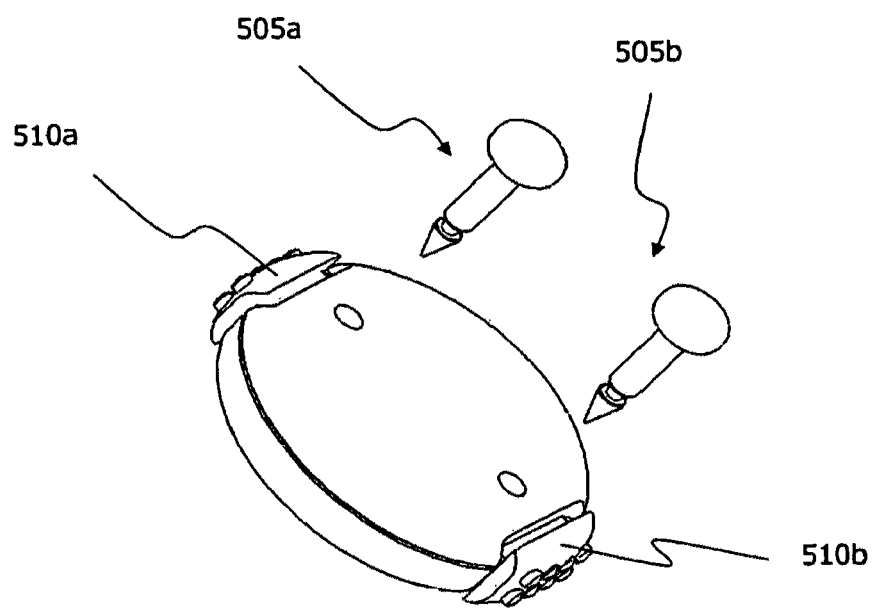
FIG. 8 shows a perspective view of the "Separate Spikes Embodiment"

FIG. 8 illustrates another embodiment of a Secure Attachment Mechanism, hereby referred to as the "Separate Spikes Embodiment". This embodiment comprises two spikes (505a, 505b) separate one from the other. Similar to the Generalized Sliding Sockets Embodiment, this embodiment utilizes sliding socket members, and release of the spikes (505a, 505b) is performed by pressing both pads (510a, 510b).

Once again, this structure conforms to the definition of the Secure Attachment Mechanism as was stated above.

Turning Spikes Embodiment

FIGS. 9A to 9D illustrate a sixth embodiment of a Secure Attachment Mechanism, hereby referred to as the "Turning Spikes Embodiment".

The spikes 605 of this embodiment have a bulge 607 of a certain shape. The sockets 609 of this embodiment are affixed to the casing 103, and have an opening 611 matching said shape.

Figure 9A:
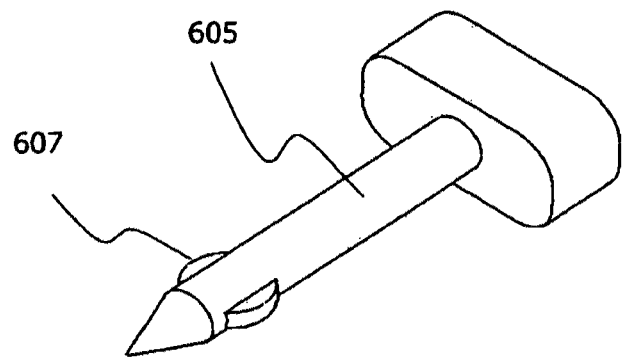
FIGS. 9A to 9D show perspective views of the "Turning Spikes Embodiment"
Figure 9B:
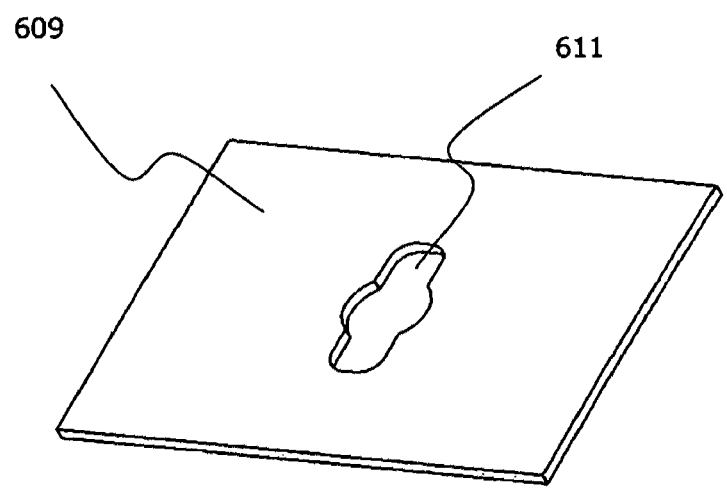
Figure 9C:
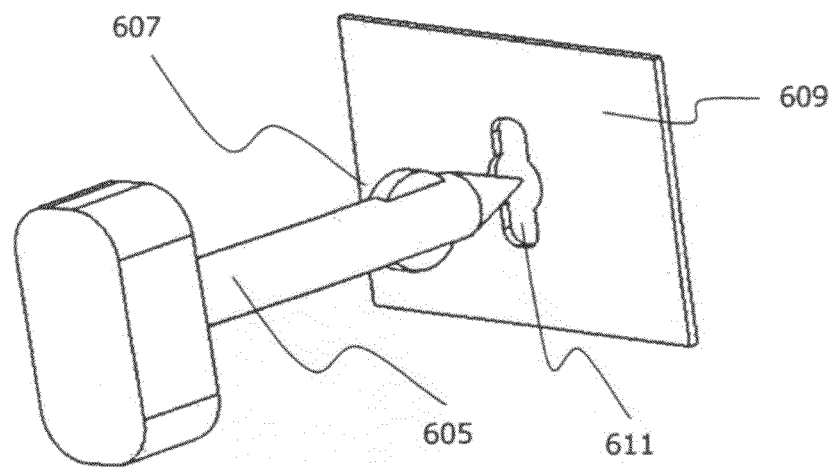
Figure 9D:
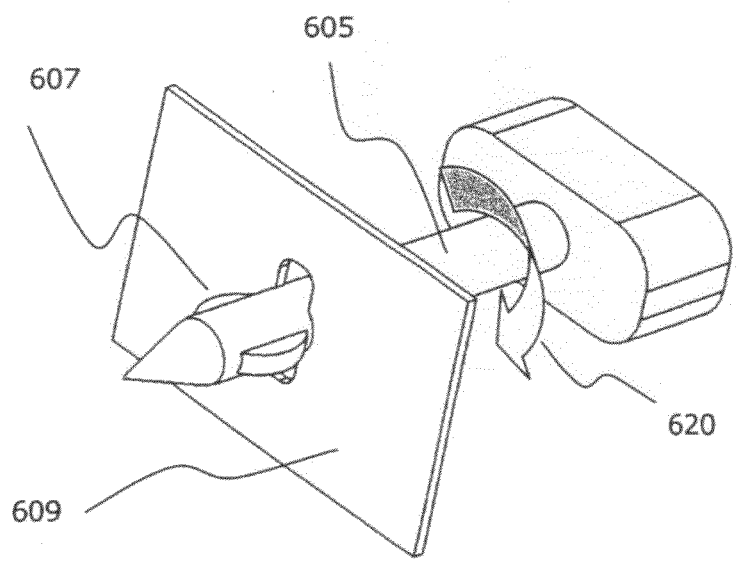

The bulge 607 can be inserted into the opening only when both shapes are aligned, as shown in FIG. 9C.

After insertion, the spikes are turned so the shapes are misaligned, thus preventing the spike from moving backward.

In this locking state, the attachment of the device to the diaper is secured, and the diaper is ready to be worn.

In order to detach the device, the diaper must be first taken off the body. Then, the spikes have to be turned back, as shown by arrow 620 in FIG. 9D.

This structure, too, conforms to the definition of the Secure Attachment as was stated above.

Once again, such a complex combination of operations, performed in the right order, requiring application of two forces for turning the spikes, then another force for pulling the locker, must be made intentionally and by a skilled user, and can never be accomplished by a baby or just happen by chance.

Embodiments suggesting a threaded spike screwed into a threaded socket member are considered to be equivalent to the Turning Spikes Embodiment presented above and fall within the spirit and the scope of this invention.

Flexible Locker Embodiment

FIGS. 10A to 10E illustrate another embodiment of a Secure Attachment Mechanism, hereby referred to as the "Flexible Locker Embodiment".

The device comprises a casing 103 (FIG. 2B) and a locker 704. The locker 704 comprises two spikes (705a, 705b respectively), and a bridge member 706. The bridge member holds the spikes apart at a certain distance. The spikes have recesses (707a, 707b respectively) facing opposite directions.

Figure 10A:
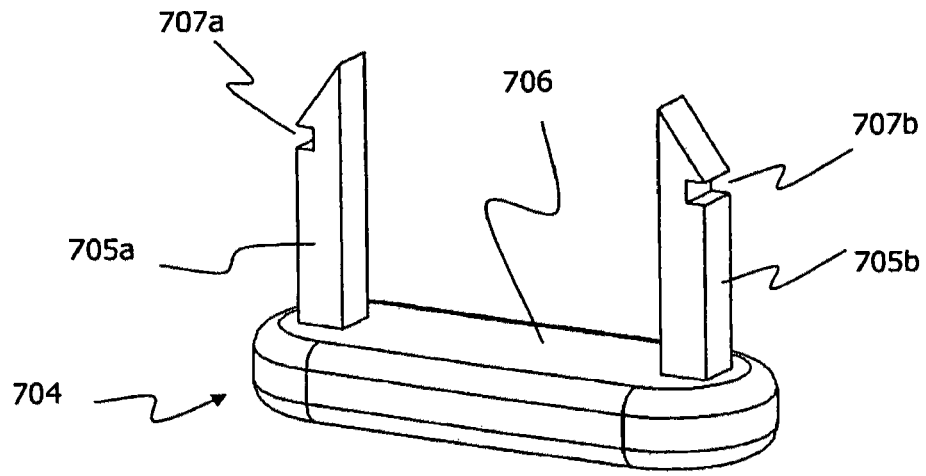
FIGS. 10A to 10F show perspective views of the "Flexible Locker Embodiment" and variations thereof.
Figure 10B:
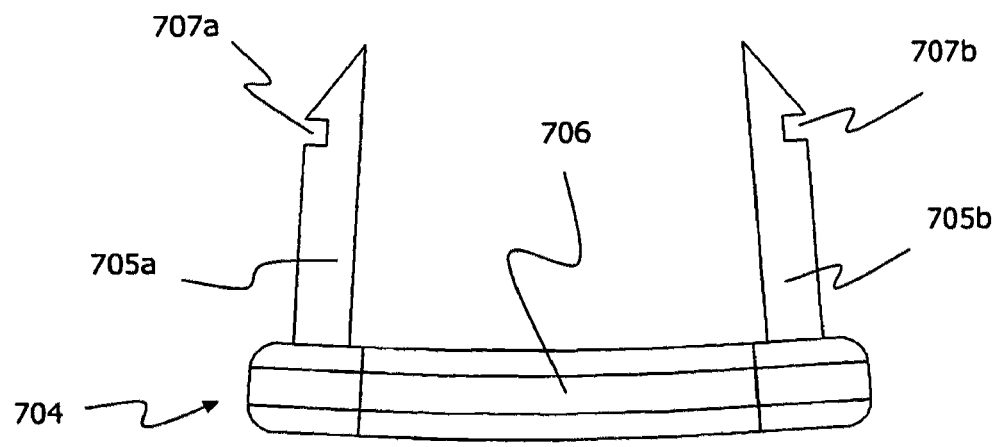

The bridge member 706 is flexible. This allows the locker 704 to be bent, as shown in FIG. 10B.

Figure 10C:
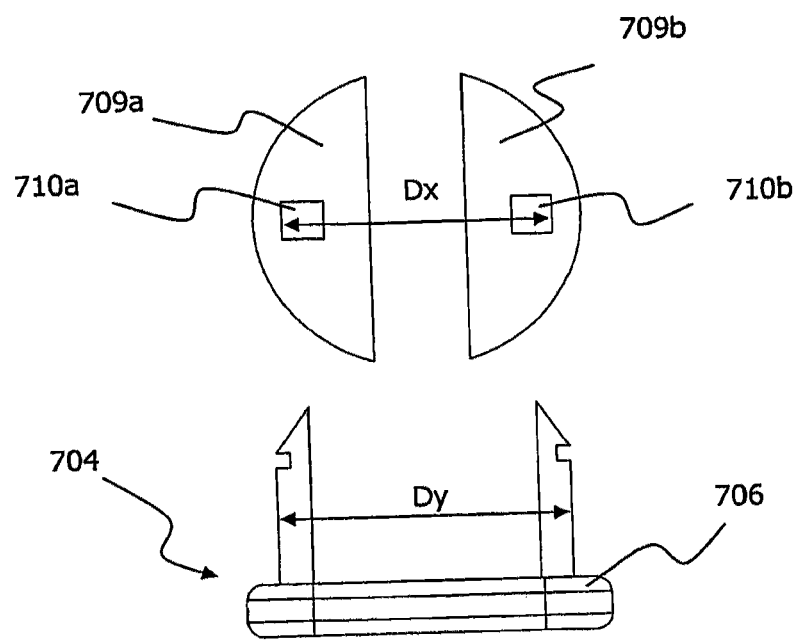

The casing 103 comprises two socket members (709a, 709b respectively), affixed within its interior. Each socket member has an opening (710a, 710b respectively). The socket members are positioned within the casing, so that the distance between the outer edges of the openings is smaller than the distance between the outer edges of the spikes (Dx<Dy as shown in FIG. 10C).

Two key members (711a, 711b in FIG. 10E) are also installed in the casing 103. Each key member is adapted to move, and is attached in one end to a releasing pad (712a, 712b respectively). The pads extend on the sides of the casing.

Figure 10D:
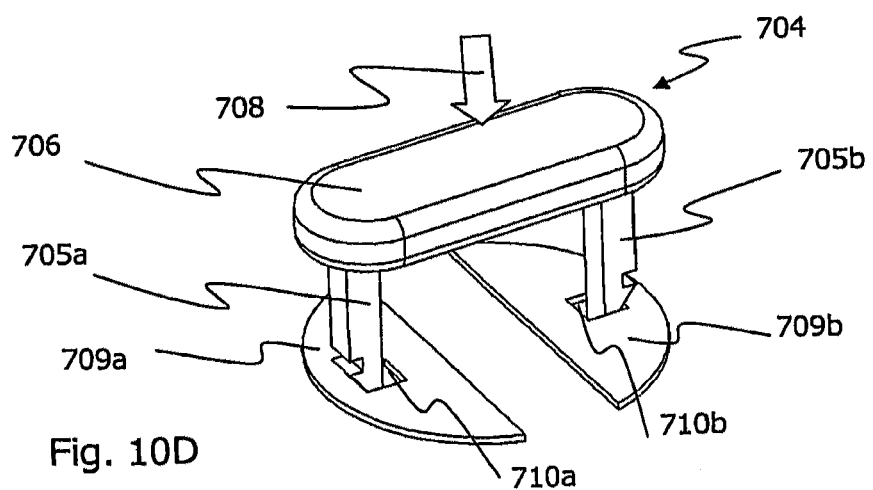

For obtaining attachment, the locker 704 is pushed forward, as illustrated by the arrow 708 in FIG. 10D. The diagonal edges of the spikes slide against the openings (710a, 710b), thus forcing the elastic bridge member 706 to bend. Eventually the spikes 705a, 705b pass through the openings 710a, 710b. When the recesses are aligned with the socket members 709a, 709b, they become interlocked, as the force of elasticity pushes the spikes 705a, 705b away from each other.

In this locking state, the spikes are prevented from moving backward, and the attachment of the device to the diaper is secured, and the diaper 102 (FIG. 1) is ready to be worn.

Figure 10E:
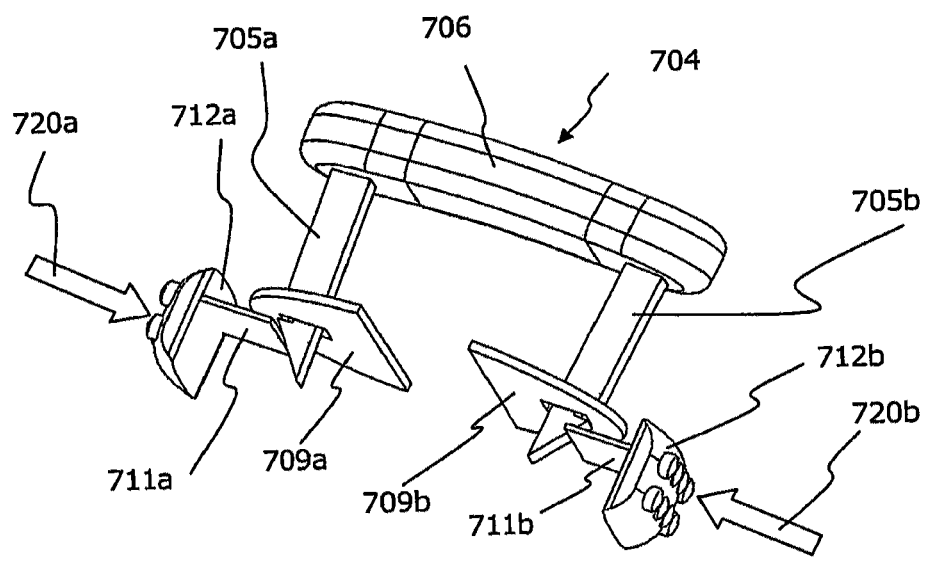

In order to release the spikes, the user must simultaneously press both pads (712a, 712b respectively), in the directions of the arrows (720a, 720b respectively) shown in FIG. 10E. The keys (711a, 711b) push the tips of the spikes, until each spike can move backward. This allows the casing 103 to be released from the locker 704 and from the diaper too.

This arrangement, too, conforms to the Secure Attachment Mechanism definition stated above.

Once again, such a combination of complex operations, performed in the right order, requiring two simultaneous forces for pressing the key members, then another force for pulling the locker 704, must be made intentionally and by a skilled user, and can never be accomplished by a baby or just happen by chance.

Figure 10F:
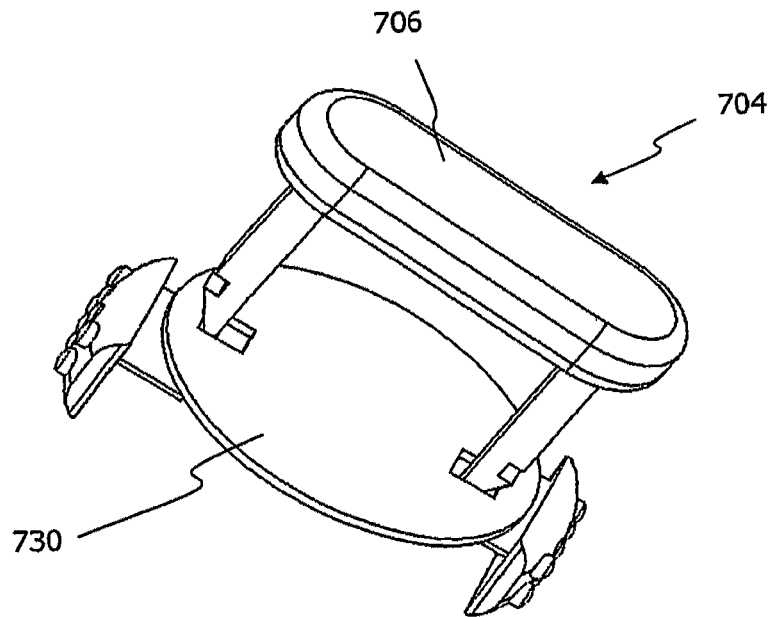

An embodiment suggesting a single socket member (730 in FIG. 10F) having two openings is also feasible. Still other feasible embodiments may utilize arrangements in which the recesses face other directions, instead of opposing directions. Still other feasible embodiments may utilize at least one flexible spike instead of a flexible bridging member. All such embodiments are considered to be equivalent to the Flexible Locker Embodiment presented above and fall within the spirit and the scope of this invention.

Single Casing Embodiment

In one preferred embodiment, hereby referred to as the "Single Casing Embodiment", the monitoring device is encased within a single casing, as shown in FIG. 1.

Figure 11:
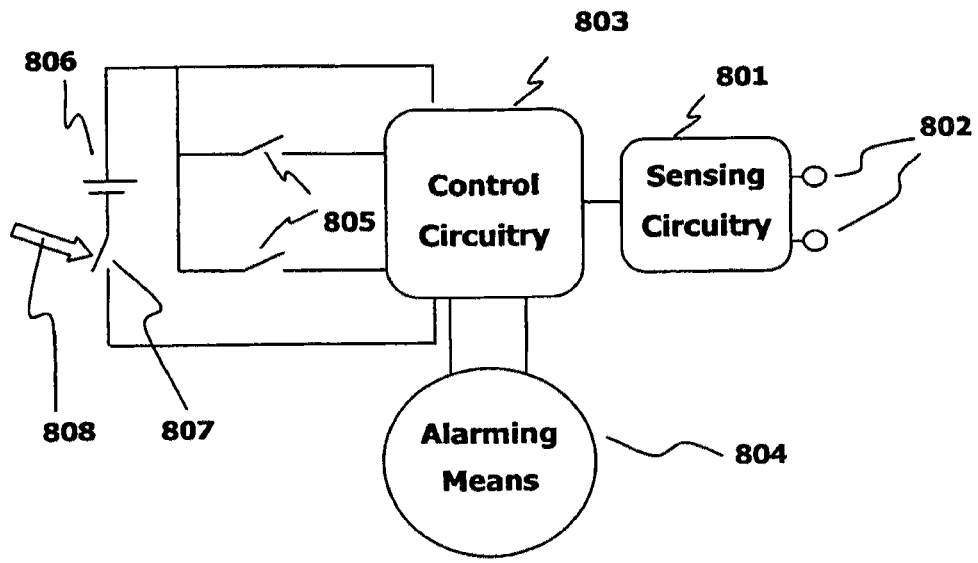
FIG. 11 shows a schematic electronic diagram of the "Single Casing Embodiment"

FIG. 11 shows a schematic electronic circuit for such an embodiment. The circuit comprises sensing circuitry 801, terminals 802 to which the socket members connect, control circuitry 803, alarming means 804, input means 805 and a power source 806. If the power source 806 is rechargeable, then a charging circuitry may also be included. This embodiment also comprises a Secure Attachment Mechanism and a casing.

The sensing circuitry 801 may comprise any combination of various sensing circuits, according to the required functionality. Such combinations may comprise of wetness sensing circuits, movement sensing circuits, temperature sensing circuits, positioning sensing circuits etc.

The control circuitry 803 may comprise timing components, input and output circuitries, together with a programmable controller, having memory and appropriate programs stored thereto, to collectively perform the operations required for achieving the goals of this device. It may be implemented by an integrated circuit (IC).

The alarming means 804 may comprise audible alarms (such as a speaker or a buzzer), visual alarms (displays or LEDs) and vibrating alarms. The alarming means may be connected by soldered wires and/or by flexible conductors.

The input means 805 allow the user to select various modes of operation, such as selecting sensitivities.

System Embodiment

In still another preferred embodiment (hereby referred to as the "System Embodiment") some of the functionalities are performed by a monitoring device as described above (referred to hereinafter as the "Monitoring Device"), while other functionalities are performed by another (separate) device (referred to hereinafter as the "Remote Device"). The devices communicate wirelessly, thus forming a system. The Monitoring Device is attached to the monitored person by a secure attachment mechanism, while the Remote Device may be located anywhere within reception range.

The devices exchange messages, wirelessly. For example, upon detecting wetness, the Monitoring Device transmits a message to the Remote Device, which in turn initiates a set of alarms.

Figure 12:
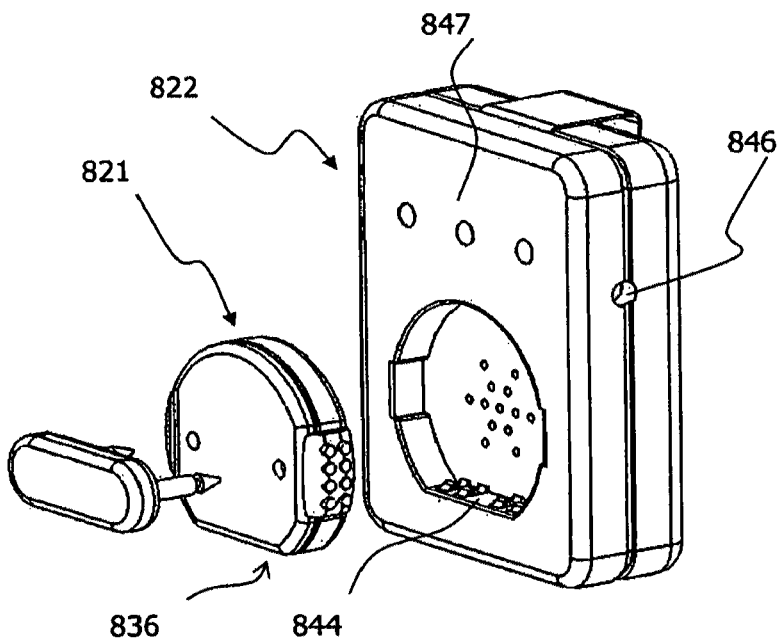
FIG. 12 shows a perspective view of the "System Embodiment"
Figure 13:
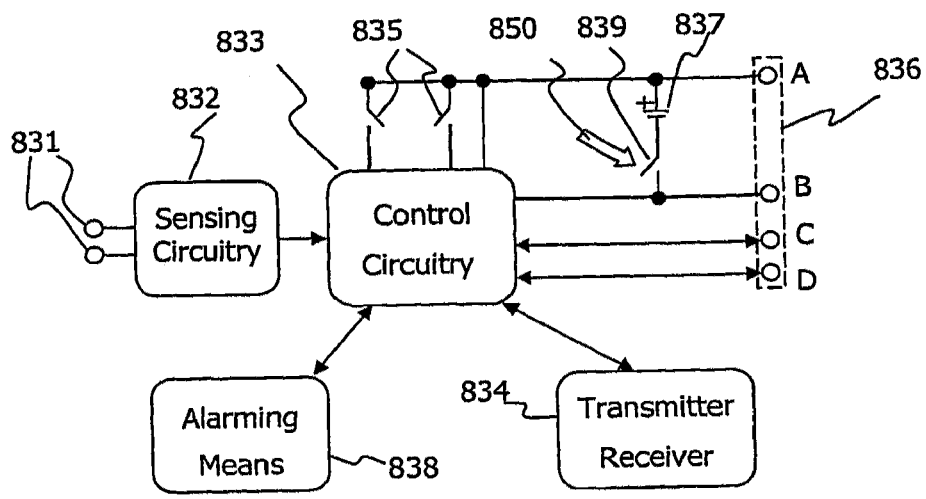
FIG. 13 shows a schematic electronic diagram of the "System Embodiment".
Figure 13:
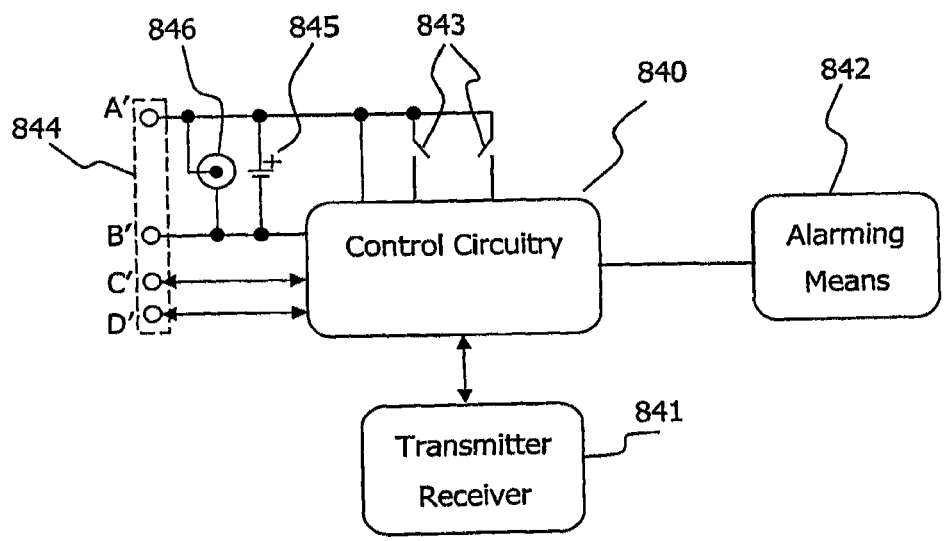

FIG. 12 shows a perspective view of the Monitoring Device 821 and of the Remote Device 822, according to an embodiment of the invention. FIG. 13 shows schematic electronic diagrams of said devices.

The Monitoring Device comprises sensing circuitry 832, control circuitry 833, wireless communication circuitry 834, input means 835, connection means 836 (with individual terminals marked as A, B, C, D) for electrical connection with the Remote Device, power source 837, alarming means 838, Secure Attachment Mechanism and a casing.

The Remote Device comprises control circuitry 840, wireless communication circuitry 841, alarming means 842, input means 843, connection means 844 (with individual terminals marked as A', B', C', D') for electrical connection with the Monitoring Device, a power source 845, connector for an external DC charger 846 and a casing.

Both control circuitries may comprise various circuits such as timing circuits, input and output circuitries, together with a programmable controller, having memory and appropriate programs stored thereto, to collectively perform the operations required for achieving the goals of this system. They may be implemented as integrated circuits (IC).

The sensing circuitry 832 may comprise any combination of various sensing means and circuits, according to the required system functionality. Such combinations may comprise wetness sensing circuits, movement sensing circuits, temperature sensing circuits, positioning sensing circuits, microphone, camera and the like.

The Alarming means (838, 842) may comprise audible alarms (such as a speaker or a buzzer), visual alarms 847 (LEDs or displays) and vibrating alarms.

The wireless communication circuits (834, 841) of both units (821, 822 respectively) may be implemented as ICs.

Some embodiments may utilize wireless communication standards, such as Zigbee or Bluetooth, and commercially available hardware devices implementing the same.

The power sources of both devices 837, 845 are rechargeable. The Remote Device 822 is charged directly from the DC charger through connector 846. However, in order to charge the Monitoring Device 831, it must be docked onto the Remote Device 832. While docked, its connection terminals 836 make contact (electrically) with the connection terminals 844 of the Remote Device. Only two of these terminal pairs (A, B) are required for delivering the DC power between the devices. The other terminal pairs (C, D) are used for establishing identity according to the PARI procedure, as will be further discussed hereinafter.

PARI

The Monitoring Device 821 and the Remote Device 822 need to communicate as a system (pair), without interrupting or being interrupted by other systems (pairs) operating within the RF range and on the same frequency. In order to achieve this, each pair assumes random identity, according to a Procedure for Assuming Random Identity referenced herein as "PARI".

Definition: PARI is a procedure, according to which two distinct devices, operating as a system, assume an identity number (hereinafter "IDN"), wherein one device randomly selects a number, then makes it known to the other device, at times when both devices are electrically connected.

Upon docking the Monitoring Device 821 onto the Remote Device 822, one device randomly selects an integer number from a very large range of numbers (e.g. between 1 and $2^{128}$). It then makes this number known to the other device via terminals C and D. This number becomes the IDN of this pair until the next docking event. It doesn't matter which device initiates the procedure.

The IDN serves to identify messages transmitted wirelessly between said devices. It is included in every message transmitted (by RF) between the devices (in both directions). Indeed, this message will be received by all the devices that operate within the RF range, however only the device having the same IDN will respond.

The chance that the same IDN will be selected by more than one pair is minimal, since the selection range is very large. If such a rare situation does happen, it will be automatically rectified when either one of said pairs will execute the PARI procedure again.

Automatic Shutdown

The locker 104 may serve as a means for automatically disconnecting the power source of the device 806 (or of the sensing unit 837). The locker (shown symbolically as arrow 808 in FIG. 11 and as arrow 850 in FIG. 13) closes a switch (807, 839) when interlocked, thus connecting the power source to the rest of the circuitry. Detaching the locker automatically shuts the power down.

Wet Diaper Alarm

According to another preferred embodiment, the monitoring device serves as a wet diaper alarm. Detecting wetness is based on sensing conductivity variations inside the diaper.

In this embodiment the locker 104 serves two purposes, i.e. it serves the purpose of securely attaching the device to the diaper, and the purpose of placing two electrodes (the spikes 105a, 105b) within the diaper.

The spikes need to be conductive while the bridge 106 has to be non-conductive. The socket members are also conductive, and connected to nodes 802 (or 831 in a system embodiment), thus they form a part of the sensing circuitry. The spikes interlock with the socket members, thus extend the sensing circuit into the diaper's absorbent material, through which the spikes pass. The conductivity of the material between the spikes increases upon becoming wet. Said circuitry senses this conductivity change, and upon reaching a selectable threshold, it signals such a change of state to said control circuitry 803, which in turn signals an alarm.

SIDS Alarm

According to still another preferred embodiment, the monitoring device serves as a SIDS alarm. The device is attached to the baby's diaper and moves along with the baby's breathing movements. It senses changes in its orientation caused by said movements. Once irregularities in these movements are determined, the device issues an emergency alert, such as a high volume siren. Such devices can also be very useful for alerting on breathing cessation of old people or sick/wounded people.

In one preferred embodiment of this device, it employs Magneto-Resistive sensors (of the types AMR or GMR). The baby's breathing movements change the orientation of the device within Earth's magnetic field, causing changes in the magnetic flux "captured" by the sensor, thus causing changes in its resistance. The device analyses the resistance readings and alerts if any irregularities are detected.

Many alternative technologies for sensing motion could be used. Some embodiments may use motion, displacement or tilt sensors, such as those based on rolling balls, electrolyte or liquid mercury.

Other embodiments may sense motion by employing devices based on gyro, especially those known as Angular Rate Sensors, based on MEMS technology.

Still other embodiments may sense motion by using photo sensitive sensors (such as photodiode, phototransistor, passive infra-red PIR, light dependent resistor LDR and cameras), so that the device "looks" outside of the system casing. Movement of the device will cause changes in the "picture" captured.

Such devices analyze the readings of these sensors and alert if any irregularities are detected.

Abnormal Body Temperature Alarm

According to still another preferred embodiment, the monitoring device serves as an abnormal body temperature alarm.

High fever may cause brain damage especially to babies. On the other hand, if body temperature drops too low it may be critical as well.

The device is attached to the external side of a diaper, thus sensing the temperature there. A suitable algorithm can use this temperature to determine whether the actual body temperature has reached a selectable threshold, whereby the device issues an alert.

Many technologies are commercially available which can be used for measuring temperature, thus they will not be discussed here further.

Paging a Lost Child

It is quite common for a toddler to stray away from his caregiver. Still another embodiment of this invention allows the caregiver to locate the child, by simply pressing a button on the Remote Device. This will cause the Monitoring Device to play an alarm, thus revealing the location of the lost child.

Other Embodiments

Having described several preferred embodiments of the invention in rather full detail, it is apparent that the monitoring devices of the present invention are applicable to a wide variety of situations.

It is understood that various changes and modifications that are obvious to a person skilled in the art to which the invention pertains, even if not shown or specifically described herein, are deemed to lie within the spirit and scope of the present invention.

Even though the description above contains specificities, they should not be construed as limiting the scope of the invention, but as merely providing illustrations of some of the presently preferred embodiments of this invention.

The invention claimed is:

1. A device for monitoring the condition of a person, comprising:
   a casing;
   electronic circuitry; and
   at least one secure attachment mechanism, each comprising a first member which is capable of moving in a forward direction up to a locking state, at which the first member is interlocked by at least one second member, so that said first member cannot be moved backward by applying a first backward force, unless said interlock is unlocked by applying at least one second force independent of said first force, and wherein said first member is a spike, having at least one recess, and wherein at said locking state said second member is introduced into said recess, thereby preventing said spike from moving backward; and
   wherein: A. said second member is a socket member having a flat surface with an opening which is large enough for said spike to pass though; B. said socket member is capable of moving so that its flat surface coincides with a virtual plane which is perpendicular to said forward direction; C. said socket member, when at rest is so positioned, by means of an elastic member that applies to it a biasing force, to enable a tip of said spike to enter through said opening while said spike moves forward, and wherein said socket member prevents backward movement of said spike at the locking state; D. said spike is positioned such that during moving forward, a diagonal portion of said spike gradually pushes said socket member against said biasing force, up to said locking state, at which said biasing force pushes the socket member into said recess; E. an edge of said recess, facing said socket member at said locking state, is substantially perpendicular to said backward direction; and F. said second force is required for retracting said socket member out of said recess, against said biasing force.

2. A device for monitoring the condition of a person, comprising:
   a casing;
   electronic circuitry; and
   at least one secure attachment mechanism, each comprising a first member which is capable of moving in a forward direction up to a locking state, at which the first member is interlocked by at least one second member, so that said first member cannot be moved backward by applying a first backward force, unless said interlock is unlocked, by applying at least one second force, independent of said first force, and wherein said first member is a spike, having at least one recess, and wherein at said locking state said second member is introduced into said recess, thereby preventing said spike from moving backward, and
   wherein: A. said second member is a flat elastic socket member in which there is an elongated opening, shaped such that it forms at least one spring member; B. the width of said opening, at a point designated for said spike to enter, is smaller than the width of said recess; C. said socket member is affixed at one of its ends to said casing; D. said spike is positioned so that during moving forward and entering said opening, said spike gradually bends said spring member, thus causing the opening to gradually increase, up to said locking state, at which the spring member is introduced into said recess; and E. said second force is required for further bending said socket member until said opening is large enough to enable release of said spike.

3. A device for monitoring the condition of a person, comprising:
   a casing;
   electronic circuitry; and
   at least one secure attachment mechanism, each comprising a first member which is capable of moving in a forward direction up to a locking state, at which the first member is interlocked by at least one second member, so that said first member cannot be moved backward by applying a first backward force, unless said interlock is unlocked, by applying at least one second force, independent of said first force, and wherein said first member is a spike, having at least one recess, and wherein at said locking state said second member is introduced into said recess, thereby preventing said spike from moving backward, and wherein: A. said second member is an elastic member having a first end affixed to said casing, and a moveable end, wherein moving the moveable end in a plane perpendicular to the forward direction requires overcoming an elasticity force of said elastic member; B. said spike is positioned such that during moving forward, a diagonal portion of said spike gradually applies force to said elastic member, causing its movable end to move perpendicularly with respect to said forward movement, up to said locking state, at which said elastic member is introduced into said recess by said elasticity force; C. an edge of said recess, facing said elastic member at said locking state, is substantially perpendicular to said backward direction; and D. said second force is required for retracting said elastic member out of said recess, against said elasticity force.

4. A device for monitoring the condition of a person, comprising:

a casing;

electronic circuitry; and at least one secure attachment mechanism, each comprising a first member which is capable of moving in a forward direction up to a locking state, at which the first member is interlocked by at least one second member, so that said first member cannot be moved backward by applying a first backward force, said interlock is unlocked, by applying at least one second force, independent of said first force, and wherein said first member is a spike, having at least one recess, and wherein at said locking state said second member is introduced into said recess, thereby preventing said spike from moving backward, and comprising at least two secure attachment mechanisms wherein: A. said spikes are connected by an elastic bridge member at a certain distance apart one from the other; B. portions of said recesses face opposite directions; C. said second members have a form of a flat socket member, having at least one opening for receiving a corresponding spike; D. said socket members are positioned within said casing, such that the distance between the outer edges of said openings is smaller than the distance between the outer edges of said spikes; E. said spikes are positioned such that during moving forward, a diagonal portion of at least one spike is gradually pressed toward the center of its corresponding opening, thus gradually bending said elastic bridge member, up to said locking state at which the edge of said opening is introduced into said recess by the elasticity force of said bridge member; F. an edge of said recess which faces said socket member at said locking state is substantially perpendicular to said backward direction; and G. said second force is required for retracting said spikes until the edges of said openings are no longer positioned within said spikes recesses.

5. The device according to claim 1, wherein said electronic circuitry comprises: A. at least one sensing circuitry, each measuring at least one value relating to a corresponding characteristic of said person's condition, and issuing at least one signal indicative of said measurement; B. at least one alarming circuitry for activating alarm means; and C. control circuitry for accepting said signal and for activating said alarm means, if said measured value is not within a selectable range.

6. The device according to claim 5, wherein said characteristic of condition is selected from the group comprising: breathing; body temperature; heartbeat; motion; wetness; whereabouts; environmental temperature; and sound pressure in said person's surroundings.

7. The device according to claim 6, wherein said sensing of motion is performed by at least one means selected from the group comprising: anisotropic magnetoresistive (AMR) sensors, giant magnetoresistive (GMR) sensors, displacement sensors, tilt sensors, Hall-effect sensors, gyro sensors, angular rate sensors and photosensitive sensors.

8. The device according to claim 7, wherein said device is used for detecting breathing movements of said person's body, and wherein said vibrating alarm is used for stimulating said person's nervous system to restart breathing.

9. The device according to claim 2, wherein said electronic circuitry comprises: A. at least one sensing circuitry, each measuring at least one value relating to a corresponding characteristic of said person's condition, and issuing at least one signal indicative of said measurement; B. at least one alarming circuitry for activating alarm means; and C. control circuitry for accepting said signal and for activating said alarm means, if said measured value is not within a selectable range.

10. The device according to claim 9, wherein said characteristic of condition is selected from the group comprising: breathing; body temperature; heartbeat; motion; wetness; whereabouts; environmental temperature; and sound pressure in said person's surroundings.

11. The device according to claim 10, wherein said sensing of motion is performed by at least one means selected from the group comprising: anisotropic magnetoresistive (AMR) sensors, giant magnetoresistive (GMR) sensors, displacement sensors, tilt sensors, Hall-effect sensors, gyro sensors, angular rate sensors and photosensitive sensors.

12. The device according to claim 11, wherein said device is used for detecting breathing movements of said person's body, and wherein said vibrating alarm is used for stimulating said person's nervous system to restart breathing.

13. The device according to claim 3, wherein said electronic circuitry comprises: A. at least one sensing circuitry, each measuring at least one value relating to a corresponding characteristic of said person's condition, and issuing at least one signal indicative of said measurement; B. at least one alarming circuitry for activating alarm means; and C. control circuitry for accepting said signal and for activating said alarm means, if said measured value is not within a selectable range.

14. The device according to claim 13, wherein said characteristic of condition is selected from the group comprising: breathing; body temperature; heartbeat; motion; wetness; whereabouts; environmental temperature; and sound pressure in said person's surroundings.

15. The device according to claim 14, wherein said sensing of motion is performed by at least one means selected from the group comprising: anisotropic magnetoresistive (AMR) sensors, giant magnetoresistive (GMR) sensors, displacement sensors, tilt sensors, Hall-effect sensors, gyro sensors, angular rate sensors and photosensitive sensors.

16. The device according to claim 15, wherein said device is used for detecting breathing movements of said person's body, and wherein said vibrating alarm is used for stimulating said person's nervous system to restart breathing.

17. The device according to claim 4, wherein said electronic circuitry comprises: A. at least one sensing circuitry, each measuring at least one value relating to a corresponding characteristic of said person's condition, and issuing at least one signal indicative of said measurement; B. at least one alarming circuitry for activating alarm means; and C. control circuitry for accepting said signal and for activating said alarm means, if said measured value is not within a selectable range.

18. The device according to claim 17, wherein said characteristic of condition is selected from the group comprising: breathing; body temperature; heartbeat; motion; wetness; whereabouts; environmental temperature; and sound pressure in said person's surroundings.

19. The device according to claim 18, wherein said sensing of motion is performed by at least one means selected from the group comprising: anisotropic magnetoresistive (AMR) sensors, giant magnetoresistive (GMR) sensors, displacement sensors, tilt sensors, Hall-effect sensors, gyro sensors, angular rate sensors and photosensitive sensors.

20. The device according to claim 19, wherein said device is used for detecting breathing movements of said person's body, and wherein said vibrating alarm is used for stimulating said person's nervous system to restart breathing.

\* \* \* \* \*